(12) United States Patent
Coffman et al.

(10) Patent No.: US 12,415,980 B2
(45) Date of Patent: Sep. 16, 2025

(54) METHOD FOR MEMBRANE GAS TRANSFER IN HIGH DENSITY BIOREACTOR CULTURE

(71) Applicant: Boehringer Ingelheim International GmbH, Ingelheim am Rhein (DE)

(72) Inventors: Jonathan Coffman, Gaithersbury, CA (US); Scott Godfrey, Pleasanton, CA (US); Lisa Sawicki, Brisbane, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1130 days.

(21) Appl. No.: 17/283,273

(22) PCT Filed: Oct. 8, 2019

(86) PCT No.: PCT/US2019/055126
§ 371 (c)(1),
(2) Date: Apr. 7, 2021

(87) PCT Pub. No.: WO2020/076776
PCT Pub. Date: Apr. 16, 2020

(65) Prior Publication Data
US 2021/0380923 A1    Dec. 9, 2021

Related U.S. Application Data

(60) Provisional application No. 62/743,767, filed on Oct. 10, 2018.

(51) Int. Cl.
*C12M 1/00*    (2006.01)
*C12M 1/04*    (2006.01)
(Continued)

(52) U.S. Cl.
CPC ............ *C12M 29/26* (2013.01); *C12M 23/24* (2013.01); *C12M 29/10* (2013.01); *C12M 29/16* (2013.01);
(Continued)

(58) Field of Classification Search
None
See application file for complete search history.

(56) References Cited

U.S. PATENT DOCUMENTS 4,897,359 A * 1/1990 Oakley .................. C12M 23/24
261/122.1
5,110,741 A * 5/1992 Ohi ........................ C12M 23/24
261/122.1
(Continued)

FOREIGN PATENT DOCUMENTS

CN    101096639 A    1/2008
CN    101549181 A    10/2009
(Continued)

OTHER PUBLICATIONS

English abstract for CN101096639, Jan. 2, 2008.
(Continued)

*Primary Examiner* — William H. Beisner
(74) *Attorney, Agent, or Firm* — Mary Breen Smith

(57) ABSTRACT

The present invention provides improved bioprocessing systems and methods for cell culture using the improved bioreactors, e.g., batch-fed or perfusion bioreactor cell culture systems for production of monoclonal or bi-specific antibodies, which are modified to include one or more membrane gas transfer modules in place of a sparger- or microsparger-based aeration systems to better regulate the levels of critical gases in a bioreactor cell culture, e.g., the
(Continued)

dissolved levels of $O_2$ and $CO_2$, even at high cell densities, without subjecting the cells to bubble-burst associated cell death.

15 Claims, 20 Drawing Sheets

(51) Int. Cl.
    *C12M 1/21*     (2006.01)
    *C12M 1/34*     (2006.01)

(52) U.S. Cl.
    CPC ............ *C12M 41/02* (2013.01); *C12M 41/26* (2013.01); *C12M 41/34* (2013.01); *C12M 47/02* (2013.01)

(56) References Cited

U.S. PATENT DOCUMENTS

| | | | |
|---|---|---|---|
| 5,149,649 A * | 9/1992 | Miyamori | C12M 41/02 210/500.21 |
| 5,998,184 A * | 12/1999 | Shi | C12M 23/58 435/348 |
| 6,001,585 A | 12/1999 | Gramer | |
| 2003/0054544 A1* | 3/2003 | Gruenberg | C12M 29/16 435/297.2 |
| 2006/0019385 A1* | 1/2006 | Smith | C12M 29/16 435/348 |
| 2008/0305540 A1 | 12/2008 | Hickey et al. | |
| 2010/0159524 A1 | 6/2010 | Smith et al. | |
| 2021/0380923 A1 | 12/2021 | Coffman et al. | |

FOREIGN PATENT DOCUMENTS

| | | |
|---|---|---|
| CN | 101831382 A | 9/2010 |
| CN | 202576435 U | 12/2012 |
| CN | 203280815 U | 11/2013 |
| CN | 106540345 A | 3/2017 |
| CN | 106754259 A | 5/2017 |
| JP | 58116678 A * | 7/1983 |
| JP | 60234580 A * | 11/1985 |
| JP | 10191961 A | 7/1998 |
| WO | 2012069841 A1 | 5/2012 |
| WO | 2015069943 A1 | 5/2015 |
| WO | 2017066725 A1 | 4/2017 |
| WO | 2020076776 A1 | 4/2020 |
| WO | 2023196391 A1 | 10/2023 |

OTHER PUBLICATIONS

English abstract for CN101549181, Oct. 7, 2009.
English abstract for CN106540345, Mar. 29, 2017.
English abstract for CN106754259, May 31, 2017.
English abstract for CN202576435, Dec. 5, 2021.
English abstract for CN203280815, Nov. 13, 2013.
English abstract for JP10191961, Jul. 28, 1998.
Engler et.al., "Controlled gas exchange in whole lung bioreactors", Journal of Tissue Engineering and Regenerative Medicine, 2018, vol. 12, No. 1, pp. e119-e129.
Wagner et.al.,"The growth and productivity of recombinant animal cells in a bubble-free aeration system", Trends in Biotechnology, Elsevier Publications Cambridge (GB)I, 1988, vol. 6, No. 5, pp. 101-104.
International Search Report and Written Opinion for corresponding application, PCT/US2019/055126, date of mailing Jan. 16, 2020.

* cited by examiner

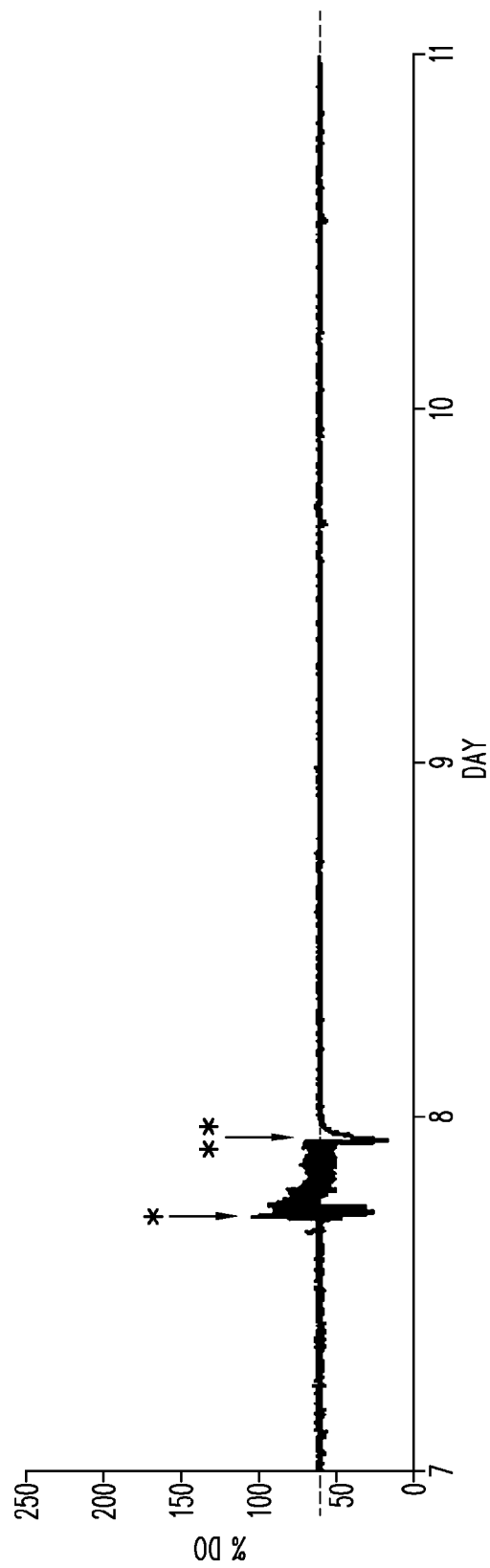

METHOD FOR MEMBRANE GAS TRANSFER IN HIGH DENSITY BIOREACTOR CULTURE

BACKGROUND

FIELD OF THE INVENTION

The invention relates generally to the field of bioprocessing, e.g., bioreactor cell culture production of monoclonal or bi-specific antibodies or other proteins of interests. The invention further relates to methods and devices for improving bioreactor cell culture conditions to achieve high density cell cultures. Still further, the invention relates to methods and devices for achieving improved gas exchange conditions in a bioreactor cell culture, thereby increasing cell culture density and product titer.

BACKGROUND OF THE INVENTION

Recent technology development has allowed cell culture to achieve very high cell density which results in high productivity of biologics, e.g., monoclonal or bispecific antibodies. [1] However, control of dissolved oxygen (DO) in these bioprocesses remains challenging as high levels of oxygen and carbon dioxide transfer are required to support high density cultures. To achieve high levels of gas transfer, methods such as microsparging, where micron-sized bubbles are released into the reactor, are employed. [2] However, the use of microsparging can increase bubble-burst associated cell death and the risk of bioreactor foam-out, which may lead to premature run termination and loss of product. [3, 4] Further, the addition of antifoams and shear protectants to prevent foam-out and bubble-burst associated cell death are in extreme cases required to be added at levels that may be toxic to cells. [5]

To eliminate challenges associated with microsparging, bubble-free aeration with porous and non-porous membranes has been investigated for cell culture applications. For example, polymeric porous membranes with micron-sized pores have been described in bubble-free aeration, where the balance of pressure between culture and gas allow bubble-free transfer at the gas-liquid interface through pores in the membrane. [6-8] In another example, the use of hydrophobic membranes (which avoids the problem of pore-wetting), have demonstrated enhanced gas transfer compared to hydrophilic membranes as liquid entrapped within pores creates an additional barrier for gas transfer to the culture. [9] Non-porous silicone polymer-based membranes (e.g., polydimethylsiloxane, PDMS) have also been used for bubble-free gas transfer, where gas molecules diffuse through the dense polymer and transfer to the culture at the membrane-culture contact surface. [110-12]

While porous and non-porous membranes have been applied in cell culture, only low densities have been achieved (i.e., <20e6 cells/mL) due to limitations in membrane design and challenges associated with membrane operation. [13] For example, in the case of porous membranes, the cell culture can be injured due to the formation of micron-sized bubbles that can emerge if the gas and culture pressures are improperly balanced with one another. Conversely, in the case of non-porous membranes, the mass transfer of gas molecules there through is slow thereby preventing sufficient gas exchange to support high density cultures.

To overcome the many challenges associated with sparging-based gas exchange processes in high-density cell culture, alternate methods and materials for bubble-free gas exchange are needed.

SUMMARY

Generally, this invention relates to bioreactors, and to bioprocessing methods using bioreactors. The present invention relates in part to the surprising finding that by replacing the sparger (e.g., used for oxygenation and/or introduction of gasses into a cell culture) of a high density cell culture bioreactor with one or more hollow-fiber membrane modules, sustained levels of dissolved oxygen (e.g., 60% DO) could be achieved at high cell densities (e.g., at least $120 \times 10^6$ cells/mL) without severe effects on culture health during operation. As a result, cells used in bioprocessing are maintained in a viable condition throughout the process, thereby increasing the productivity of a bioreactor.

In one aspect, the disclosure provides a method of culturing cells in a bioreactor comprising providing a mass transfer of a gas to/from the bioreactor without generating bubbles inside the bioreactor. In certain embodiments, the bioreactor is a perfusion bioreactor. The bioreactor can also be a batch-fed bioreactor.

In certain embodiments, the mass transfer of a gas to/from the bioreactor is provided by a gas transfer module. In various embodiments, the gas transfer module comprises a non-porous membrane, which can be, for example, a polymer, metal, or ceramic. Polymers can include silicone gum homopolymer, polydimethylsiloxane (PDMS), or silicone-polycarbonate copolymer. In various embodiments, the non-porous membrane comprises a plurality of hollow fibers.

In various embodiments, the gas transfer module comprises a first flow path through the hollow fibers for passage of one or more gases and a second flow path around the hollow fibers for a flow of cell culture media and/or cells.

In other embodiments, the gas transfer module is located outside of the bioreactor.

In certain embodiments, the plurality of hollow fibers provide a flow path for culture media and cells to travel through spaces separating the hollow fibers. The spaces can be homogenous or heterogenous. The spaces can be of sufficient size to allow passage of a cell without causing shear forces on the cell. In certain embodiments, the spaces comprise a distance of about 15 µm to about 2000 µm. In certain other embodiments, the spaces comprise a distance 15-30 µm, 20-40 µm, 30-60 µm, 40-80 µm, 60-120 µm, 80-160 µm, 100-200 µm, 150-300 µm, 200-400 µm, 200-500 µm, 200-600 µm, 200-700 µm, 200-800 µm, 200-900 µm, 200-1000 µm, or 500-2000 µm, or a combination thereof.

In various embodiments, the flow of cell culture media and/or cells comprises tangential, axial flow or a combination thereof. The flow of the cell culture media and/or cells can be at a rate that is sufficient to maintain culture homogeneity without causing shear forces on the cells.

In various embodiments, the gasses can be carbon dioxide, oxygen, or nitrogen, or other gasses or even air.

In various embodiments, the bioreactor comprises a cell density of about $20 \times 10^6$ cells/ml, about $30 \times 10^6$ cells/ml, about $40 \times 10^6$ cells/ml, about $50 \times 10^6$ cells/ml, about $60 \times 10^6$ cells/ml, about $70 \times 10^6$ cells/ml, about $80 \times 10^6$ cells/ml, about $90 \times 10^6$ cells/ml, about $100 \times 10^6$ cells/ml, about $110 \times 10^6$ cells/ml, about $120 \times 10^6$ cells/ml, about $130 \times 10^6$ cells/ml, about $140 \times 10^6$ cells/ml, about $150 \times 10^6$ cells/ml, about $160 \times 10^6$ cells/ml, about $170 \times 10^6$ cells/ml, about $180 \times 10^6$ cells/ml, about $190 \times 10^6$ cells/ml, about $200 \times 10^6$ cells/ml, about 210×10⁶ cells/ml, about 220×10⁶ cells/ml, about 230× 10⁶ cells/ml, about 240×10⁶ cells/ml, or about 250×10⁶ cells/ml.

In various embodiments, the method avoids production of foam and/or requires no anti-foaming agent during cell culture.

In other embodiments, the bioreactor comprises no headspace or substantially no headspace.

In various embodiments, the bioreactor comprises two or more gas transfer modules. The two or more gas transfer modules can provide mass transfer of different gases comprising oxygen, carbon dioxide, or nitrogen gas, and even air.

In another aspect, the specification provides a bioreactor system for high-density cell culture comprising a bioreactor vessel for growing cells in cell culture media and a liquid flow path in fluid communication with the bioreactor vessel, wherein the liquid flow path forms a circuit exterior to the bioreactor vessel for translocating cell culture media through a first and a second membrane gas transfer module.

In various embodiments, the first membrane gas transfer module is for adding oxygen to the cell culture media.

In other embodiments, the second membrane gas transfer module is for stripping carbon dioxide from the cell culture media.

In still other embodiments, the first membrane gas transfer module comprises a oxygen flow path and a cell culture medium flow path, wherein the gas flow path and cell culture flow path are separated by a gas-permeable membrane.

In still other embodiments, the first membrane gas transfer module comprises an air/carbon dioxide flow path and a cell culture medium flow path, wherein the air/carbon dioxide flow path and cell culture flow path are separated by a gas-permeable membrane.

The liquid flow path of the bioreactors described herein forms a circuit further comprising one or more additional elements, which can include a cell harvesting filter, a perfusion pump, a source of oxygen, a source of air/carbon dioxide, an oxygen sensor and/or a pH sensor.

In various embodiments of the bioreactors described herein, the cells of the high-density cell culture are at a density of about 20×10⁶ cells/ml, about 30×10⁶ cells/ml, about 40×10⁶ cells/ml, about 50×10⁶ cells/ml, about 60×10⁶ cells/ml, about 70×10⁶ cells/ml, about 80×10⁶ cells/ml, about 90×10⁶ cells/ml, about 100×10⁶ cells/ml, about 110×10⁶ cells/ml, about 120×10⁶ cells/ml, about 130×10⁶ cells/ml, about 140×10⁶ cells/ml, about 150×10⁶ cells/ml, about 160×10⁶ cells/ml, about 170×10⁶ cells/ml, about 180×10⁶ cells/ml, about 190×10⁶ cells/ml, about 200×10⁶ cells/ml, about 210×10⁶ cells/ml, about 220×10⁶ cells/ml, about 230×10⁶ cells/ml, about 240×10⁶ cells/ml, or about 250×10⁶ cells/ml.

In various embodiments, the first and second membrane gas transfer modules add and/or remove gasses to/from the cell culture medium without forming bubbles.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 4A shows that a steady-state VCD of 40e6 cells/mL was achieved in perfusion culture with spargers. After four days of steady-state operation, the microsparger in one of the reactors was turned off and $O_2$ was added through the membrane to sustain required DO (dissolved oxygen) at set point (*) and operated for three days at steady-state. After steady-state operation, the cell bleed was lowered (**) and a density of 120e6 cells was achieved using $O_2$ supplied through the membrane to control DO. FIG. 4B shows that percent viability using the membrane and traditional sparging are comparable during the course of culture. FIG. 4C shows that LDH (lactate dehydrogenase activity assay) of the bioreactor operated with membrane gas exchange matches that of the bioreactor operated with traditional sparging. The increase in LDH for the membrane culture after day 13 may be attributed to the increased cell density.

FIGS. 5A-5C show DO (dissolved oxygen) levels during culture with membrane gas exchange during steady-state and unsteady-state operation, e.g., using the bioreactor system of FIG. 1B, FIG. 1C, or FIG. 1D. FIG. 5A shows that baseline DO profile established during ramp-up to steady-state density. Microsparging started at day 1-2 (*) and stabilized by day 2-3 when a density of 40e6 cells/mL was achieved. FIG. 5B shows that the $O_2$ line was switched over to the membrane on day 7 (*). Fluctuations were controlled by adjusting the gain and integral (* to ) and a mixture of air (0.25 LPM) and $O_2$ (0.25 LPM) was sparged through the drilled hole sparger, rather than 0.5 LPM $O_2$ so that the fluctuations in DO would further stabilize as the membrane provided too much oxygen to the culture (). FIG. 5C shows that cell bleed was lowered on day 11 and density was increased to 120e6 cells/mL. Fluctuations in the DO may have been caused by wetting of the fibers and the gas outlet vent filter, causing blockage and loss of gas transfer during operation.

FIG. 6A shows that densities of ~130e6 cells/mL were reached during ramp-up to high cell density with traditional sparging, while densities of ~100×$10^6$ cells/mL were reached with membrane gas exchange. Shear from the membrane may affect culture health during ramp-up to high densities. FIG. 6B shows that cells had comparable viability for both membrane and sparger aeration during the course of culture (>85%). FIG. 6C shows that LDH was comparable for both membrane gas exchange and traditional sparging.

Higher LDH would be expected for the culture with traditional sparging due to higher cell density, indicating that the membrane exchanger may be causing shear and damage to cells during operation.

Figure 1A:
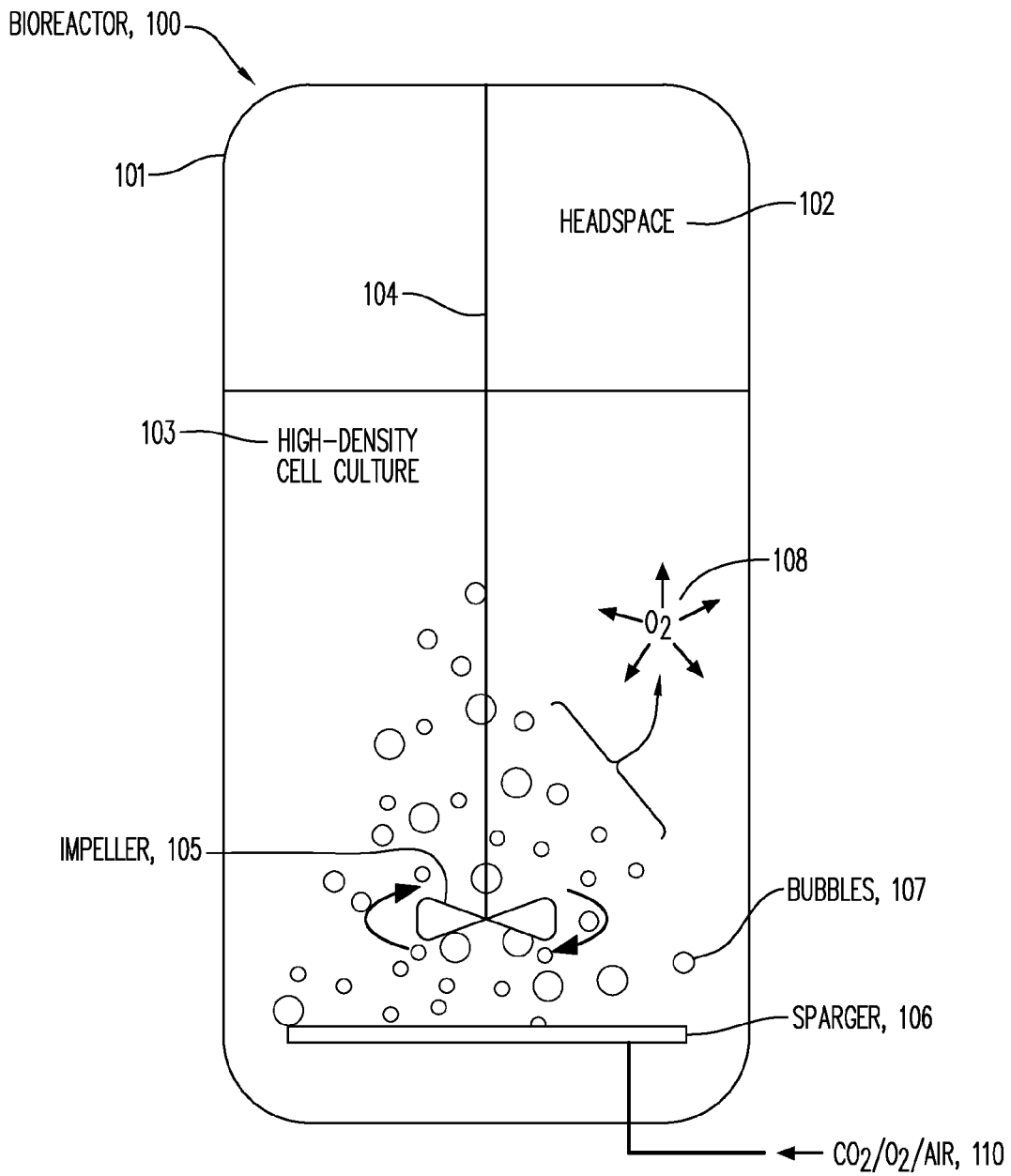
FIG. 1A provides a schematic of a bioreactor 100 known in the art comprising a sparger (or microsparger) 106 and a source of oxygen/air/carbon dioxide or other gases 110 for gas transfer to the cell culture 103. The prior art bioreactor 100 forms or produces bubbles or microbubbles 107 during the gas transfer process, which are harmful to the cells of the culture and can result in foaming, and thus, low cell density and/or cell culture product yields.
Figure 1B:
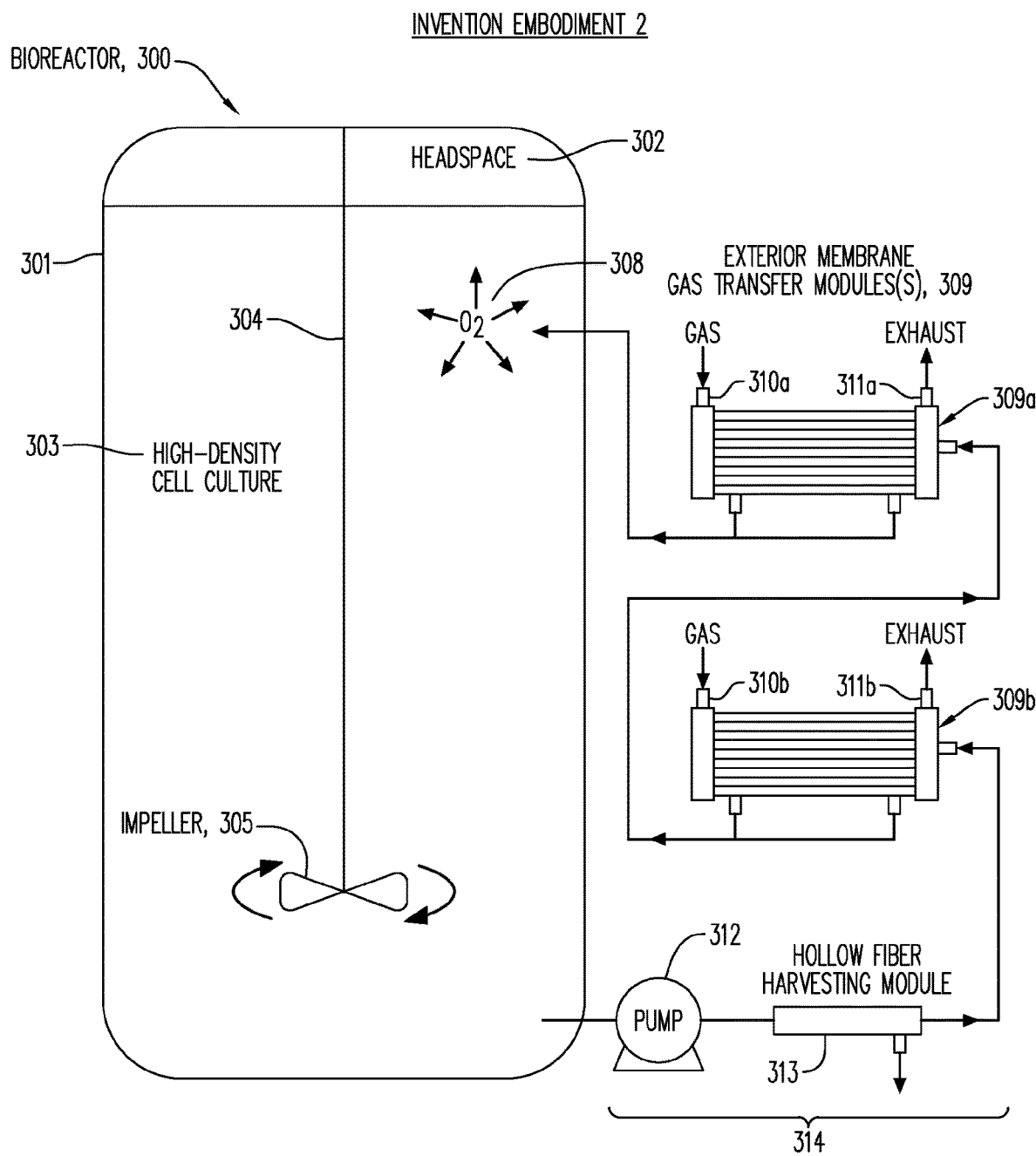
FIG. 1B shows a schematic of an embodiment of the bioreactors disclosed herein. In this embodiment, an improved bioreactor 300 includes one or more exterior-located membrane gas transfer modules 309 which are fed cell culture along a flow path 314 from/to the bioreactor in series by a pump 312. The first membrane gas transfer module 309*b* has a gas input 310*b* and gas exhaust 311*b*. The second membrane gas transfer module 309*a* also has a gas input 310*a* and a gas exhaust 311*a*. The pump 312 moves the cell culture from the bioreactor 300 along the flow path 314 (i.e., recirculation loop) through the first membrane gas transfer module 309*b* and then through the second membrane gas transfer module 309*a*, allowing the cell culture to interact with the gasses flowing through the membrane modules, which are introduced at the gas inlets and which exit out the exhaust ports. The gases interact with the cell culture by passages through the gas-permeable membranes in the modules that separate the gas flow zone from the cell culture flow path. The modules allow the addition of certain gasses (e.g., oxygen) and/or removal of other gasses (e.g., $CO_2$) from the bioreactor cell culture without the generation of bubbles. The cell culture, once treated by the modules along flow path 314, is return to the bioreactor 300. The exact configuration shown in FIG. 1B is not intended to limit other possible configurations contemplated herein. A computer controller can be included to blend $O_2$, $CO_2$, $N_2$, air, or other gas flows to the membranes to maintain dissolved $O_2$ and $CO_2$ at preferred concentrations in the bioreactor.
Figure 1C:
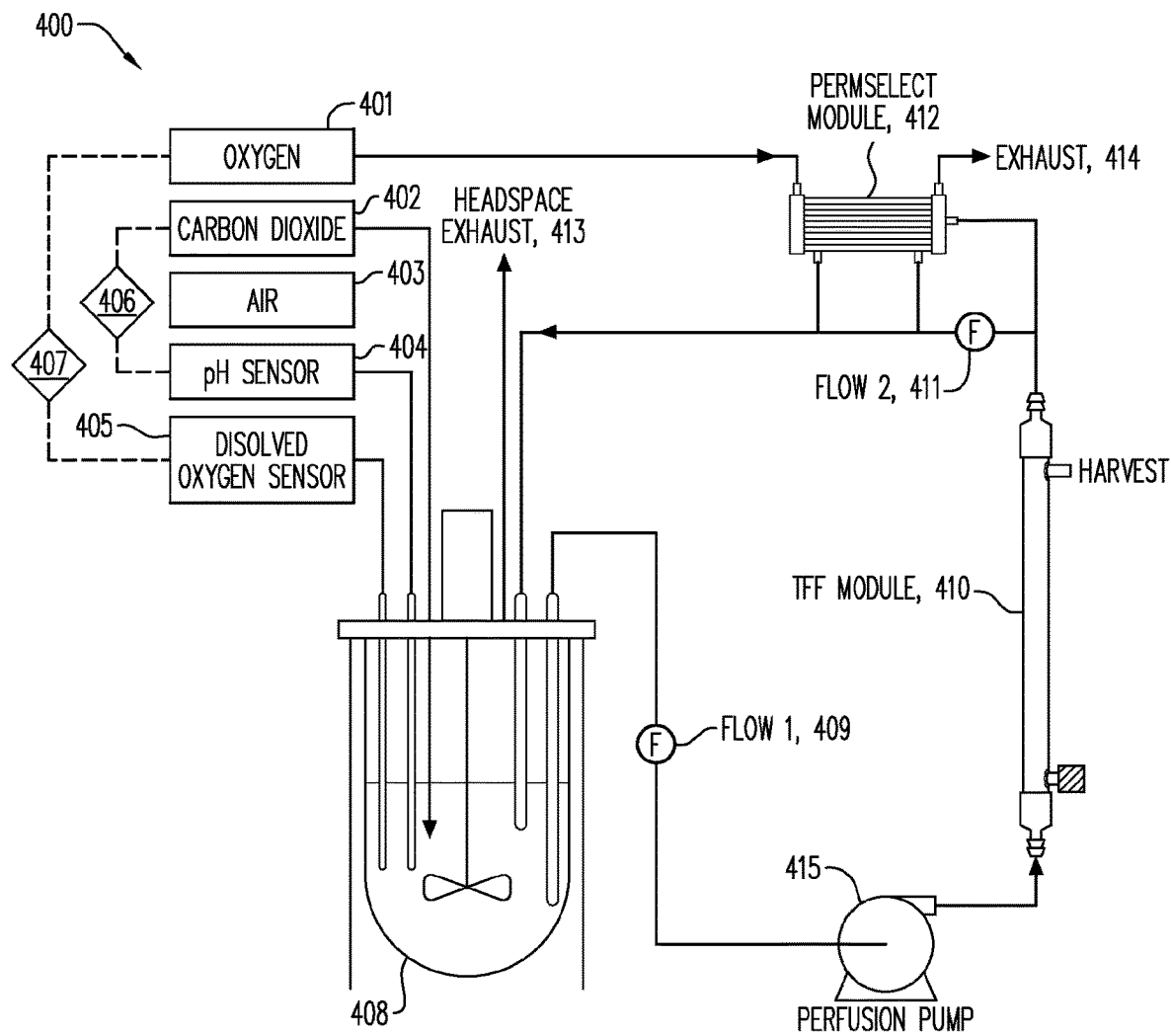
FIG. 1C shows a typical 2 liter (2 L) working volume glass stirred tank bioreactor system 400 with TFF recirculation loop (409 and 411) containing a pump 415, filter (410), and a bubble-less membrane gas transfer module (412) to replace the microsparger for high density culture. A computer controller (405 and 407) modulates $O_2$ gas flow 401 to the membrane 412 to maintain dissolved $O_2$ in solution. Carbon dioxide (402) and air (403) flows may directly feed the growth vessel 408. The pH sensor 404 is in communication with the $CO_2$ flow, which regulates the pH level of the cell culture. In operation, cell culture is removed by flow 1 (409) by the perfusion pump 415 and fed through the filter 410 (TFF module) and optionally harvested. A portion of the flow may exit the filter 410 and return to the cell culture vessel via flow 2 (411). A second portion of the flow may exit the filter 410 and enter the membrane gas transfer module 412, where it may be oxygenated by interaction with the oxygen flow 401, which may optionally be blended with air (403). Carbon dioxide may be stripped out through the exhaust 414. Carbon dioxide may also be release through the headspace exhaust 413.
Figure 1D:
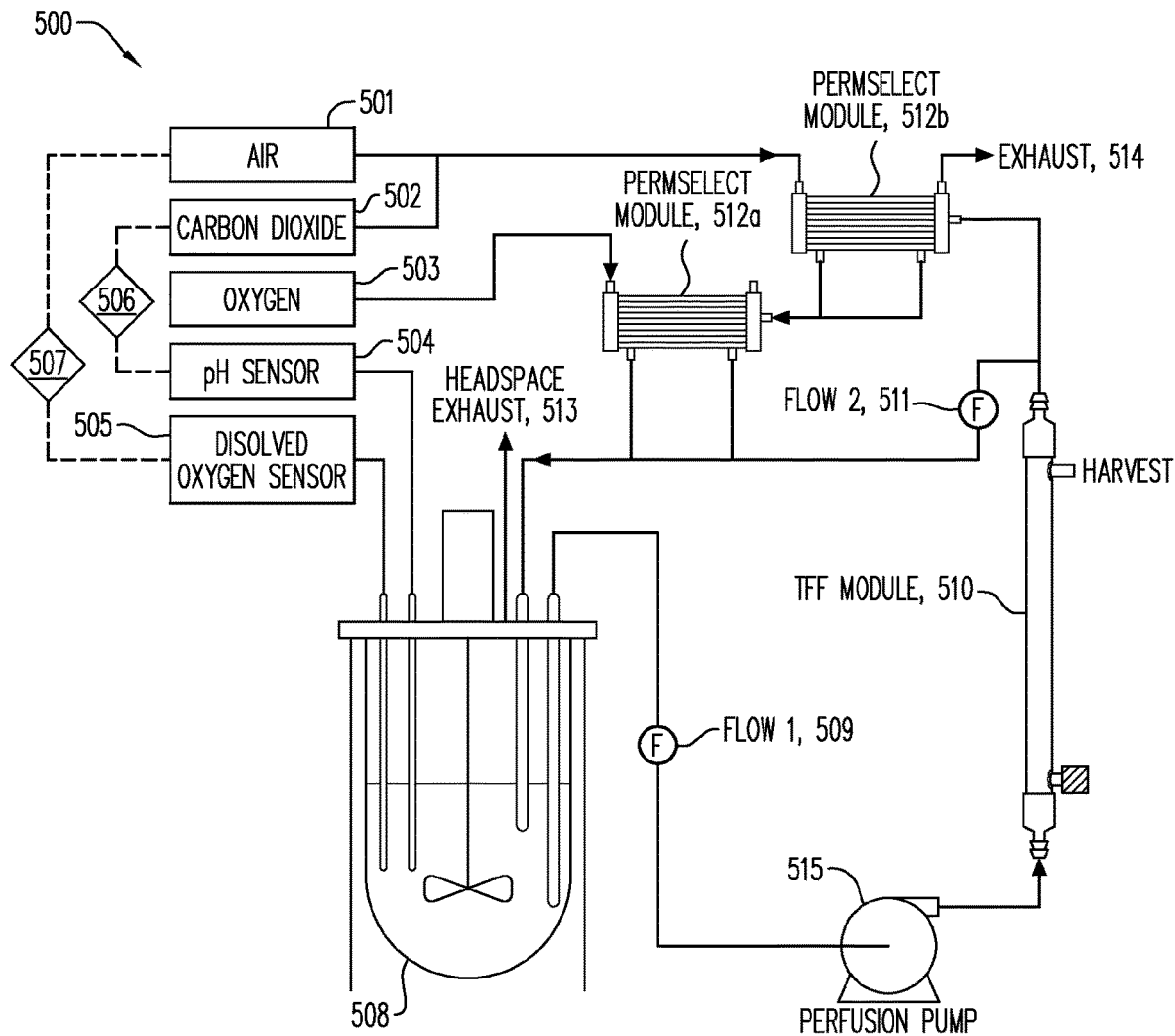
FIG. 1D shows a 2 liter (2 L) bubble-free high density bioreactor system 500, comprising a TFF recirculation loop (509 and 511 flow paths), a TFF filter 510, a pump 515, and a series of membrane gas transfer modules (512A and 512B) for adding and subtracting gasses from the high density cell culture without adding bubbles. The first module 512A functions to oxygenate the cell culture media to maintain a sustained dissolved oxygen ("DO") content or preferred concentration. The first module 512A is supplied by a flow of oxygen 503. The level of oxygen in the cell culture is measured by the dissolved oxygen sensor 505 The second membrane gas transfer module 512B functions to strip carbon dioxide from the cell culture. The second membrane gas transfer module 512B is supplied by a flow of air 501 (which contains nitrogen gas required for carbon dioxide stripping) and a flow of carbon dioxide 502. The level of flow of 501 and 502 are then controlled by pH sensor 504 and computer 506.
Figure 7A:
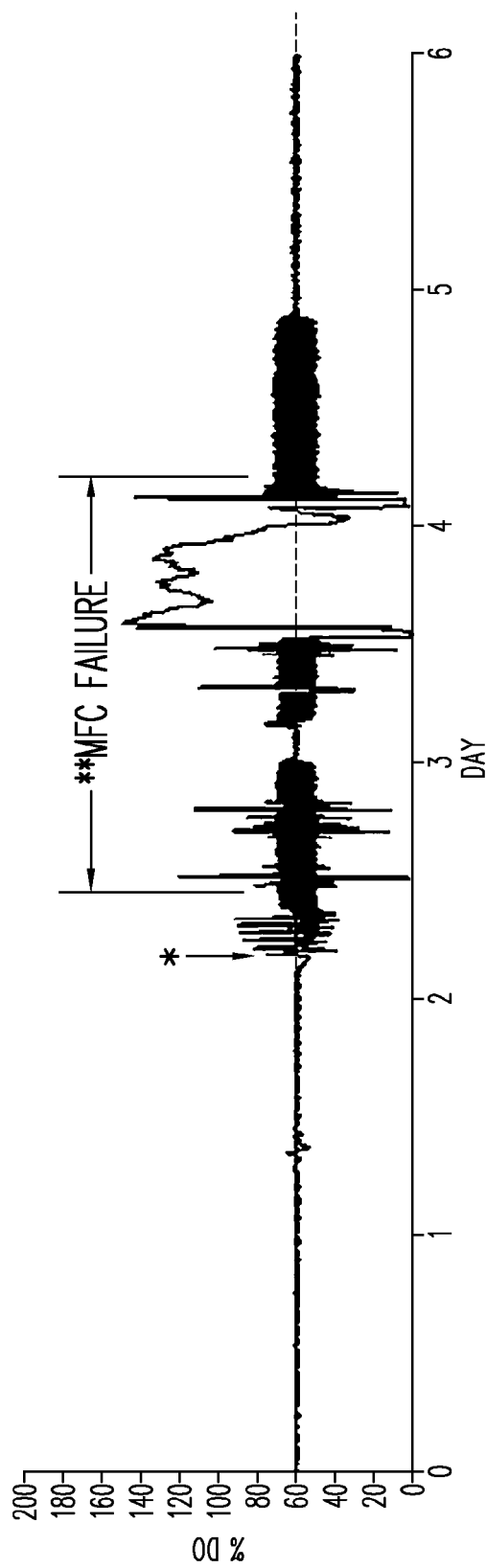
Figure 7B:
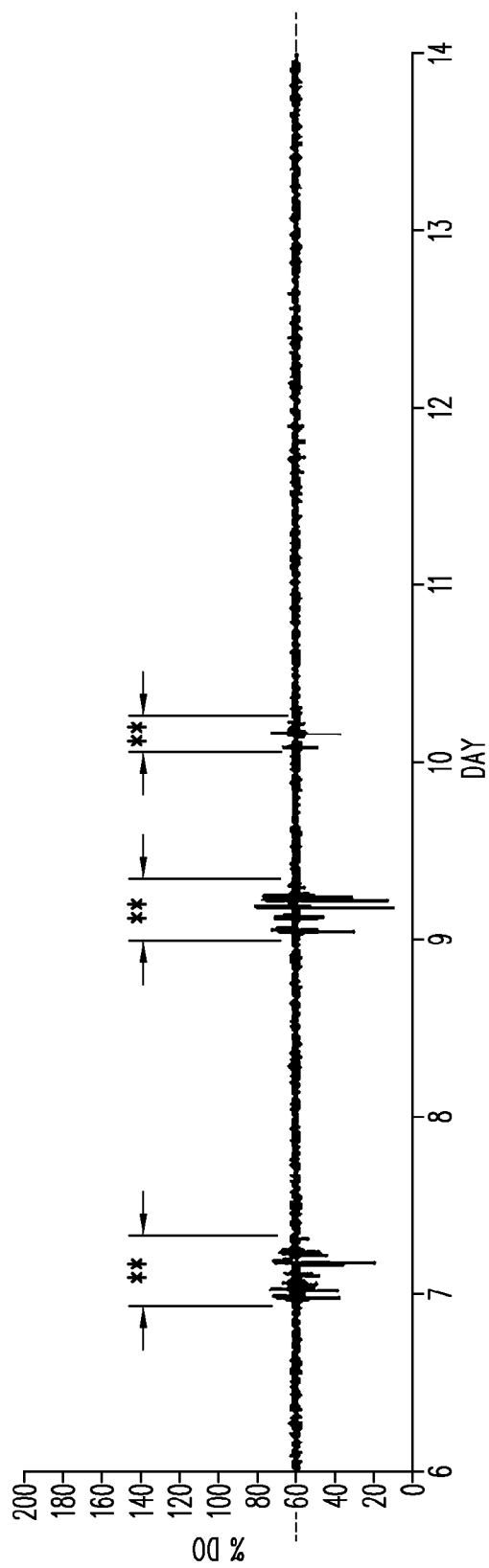

FIGS. 7A-7B show DO control during ramp-up to high cell densities using a bioreactor system of FIG. 1B, FIG. 1C, or FIG. 1D. FIG. 7A shows that initially, DO is controlled with sparging through the drilled hole sparger. As density increases, additional $O_2$ is sent through the membrane to sustain DO at 60% (*). MFC failure led to wide fluctuations and issues controlling DO during the membrane startup phase. Once control was restored to the MFC, DO fluctuated around setpoint, eventually reaching steady operation day 6-7 at cell densities around 80e6 cells/mL. FIG. 7B shows that at peak densities, DO control through the membrane remained stable, with several fluctuations occurring during temporary MFC failure.

Figure 8A:
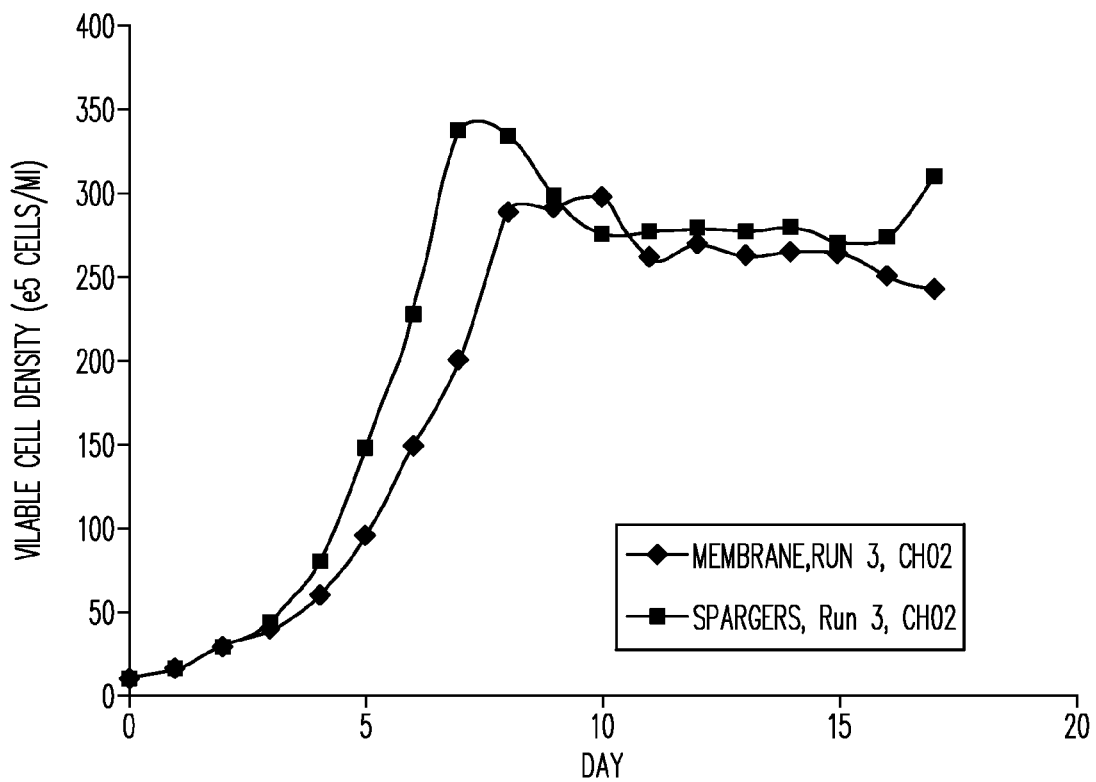
Figure 8B:
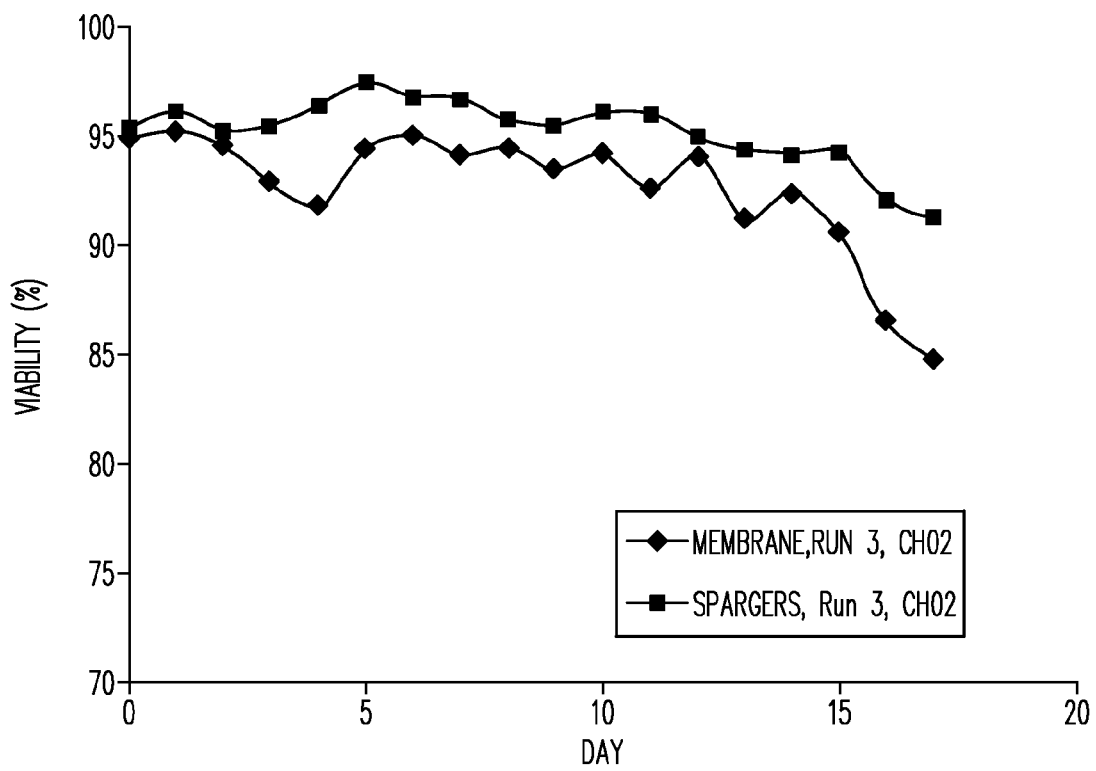
Figure 8C:
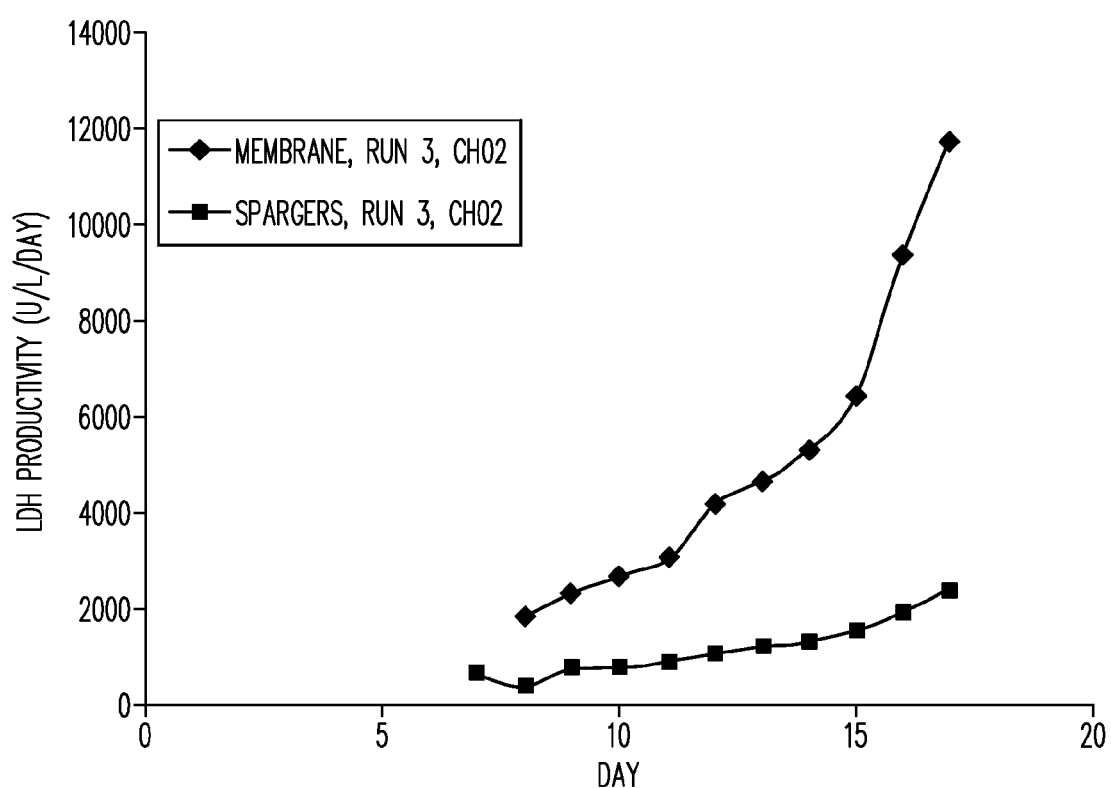

FIGS. 8A-8C show VCD (viable cell density), percent viability, and LDH (lactate dehydrogenase activity assay) of CHO2 cells cultured in a bioreactor operated with membranes for bubble-free aeration, e.g., using a bioreactor system of FIG. 1B, FIG. 1C, or FIG. 1D. FIG. 8A shows that viable cell densities of 25-30e6 cells/mL were achieved for weeks in culture. Membrane cultures took an additional day to reach steady-state operating density indicating there may be some effect of the membrane on the culture health. FIG. 8B shows that the viability of the membrane cultures was comparable to, but slightly lower than traditional sparging, further indicating effects of membrane on the cells. FIG. 8C shows that the LDH of the membrane culture was higher than the bubble-sparged bioreactor, indicating that cell shear and lysis may occur due to the densely-packed fibers in the current membrane unit design.

Figure 9A:
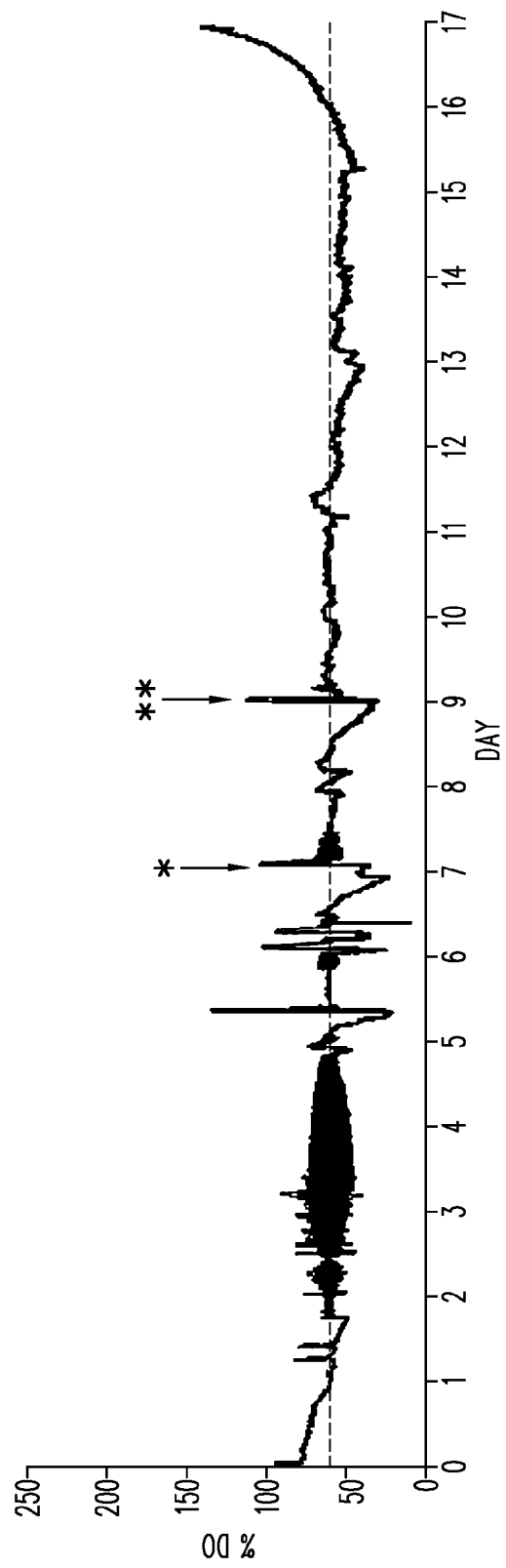
Figure 9B:
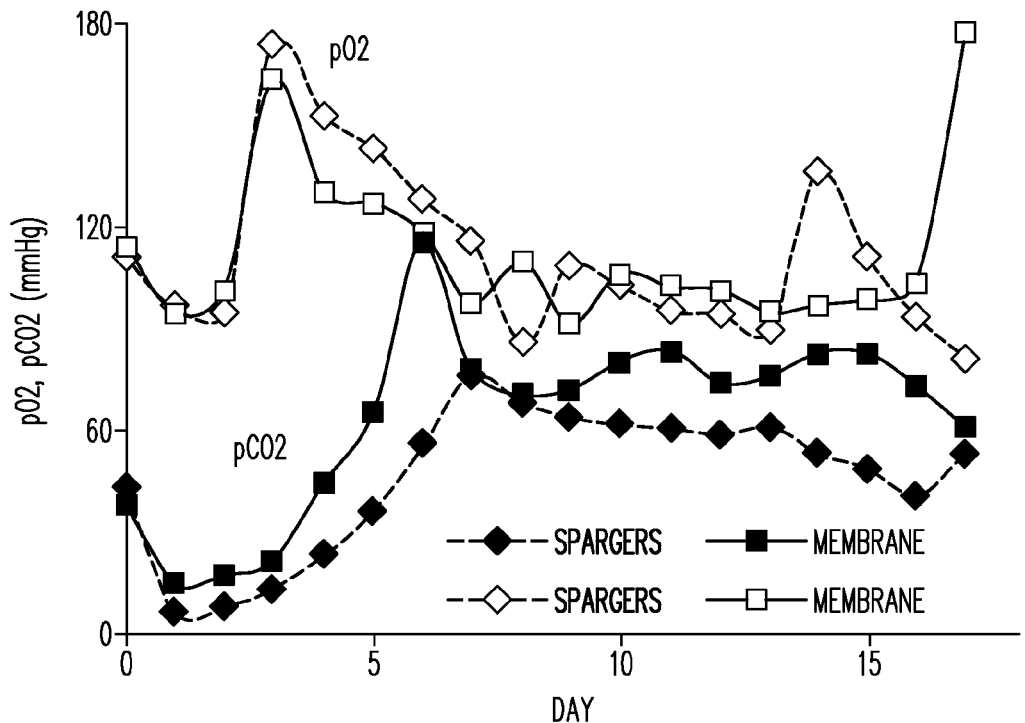

FIGS. 9A-9B shows DO (dissolved oxygen) control with bubble-free gas exchange through silicone-based membranes, e.g., using a bioreactor system of FIG. 1B, FIG. 1C, or FIG. 1D. FIG. 9A shows DO controlled around 60% during culture supporting CHO2 densities of 25-30e6 cells/mL. On day 7, recirculation was increased to support oxygen demand at high cell density (*). On day 9, control was switched to manual for better control over fluctuations in DO (**). FIG. 9B shows daily $pO_2$ and $pCO_2$ readings monitored offline during the entire culture period, demonstrating comparable levels of dissolved oxygen in cultures controlled with sparging or membrane gas exchange. Note that the increase in $pCO_2$ at Day 6 was likely due to 100% pure $O_2$ flow to both membranes. To address high $pCO_2$, air was mixed with $O_2$ through the first sparger and $pCO_2$ returned to levels comparable to the sparger cultures.

Figure 10:
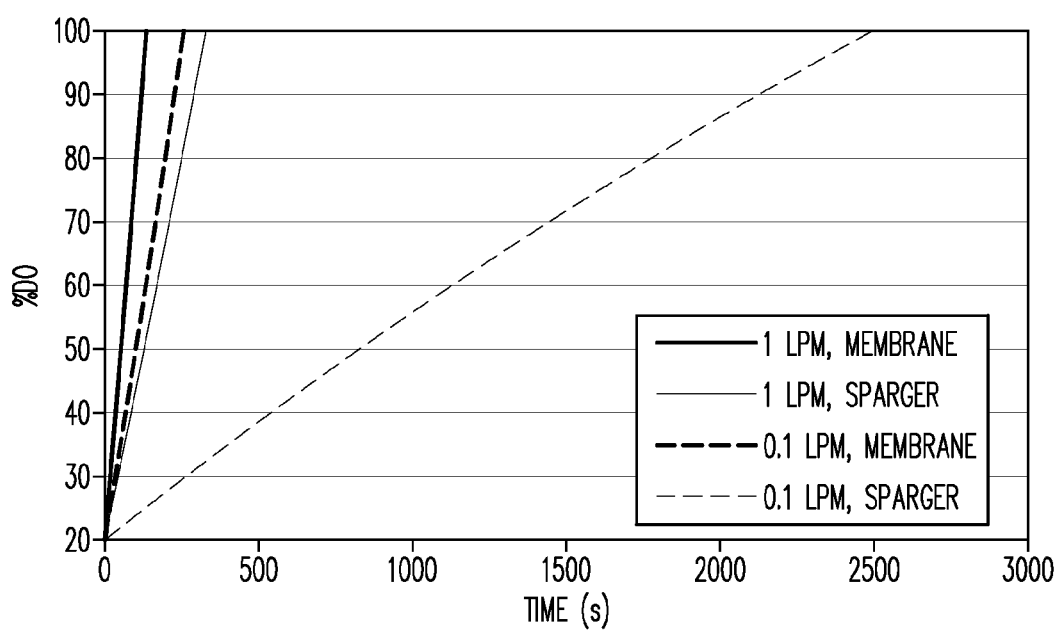

FIG. 10 shows an initial test for $O_2$ transfer with a bioreactor system of FIG. 1B, FIG. 1C, or FIG. 1D configured having a 100 L volume filled with 65 L of water as compared to a state-of-the-art bioreactor of FIG. 1A. More rapid gas transfer was observed with the membrane-based bioreactors as compared to the built-in sparger system.

Figure 11:
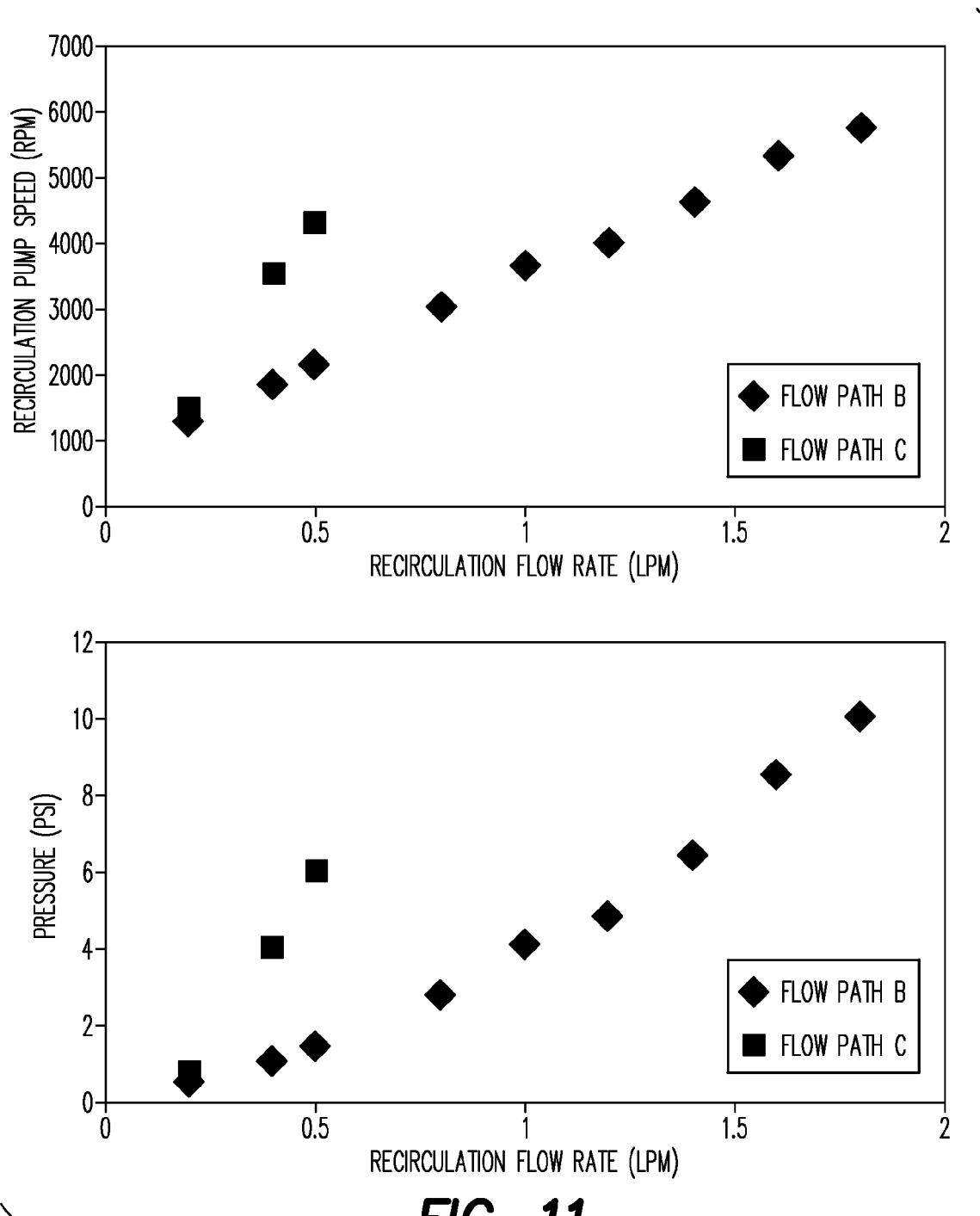

FIG. 11 shows that pump speeds are higher for a flow path represented by FIG. 3C to achieve similar flow rates run in a flow path represented by FIG. 3B, indicating restrictions in flow path C (top graph). These restrictions result in higher pressures observed in the flow path C (bottom graph).

DETAILED DESCRIPTION

Provision of oxygen is a key factor in cellular aerobic metabolic processes as it is the primary electron acceptor during energy synthesis. Ensuring an efficient supply of dissolved oxygen is the greatest challenge facing the operation of a cell culture bioreactor, and in particular, for high-density cell culture bioprocesses common in commercial production scenarios, e.g., clinical production of monoclonal or bi-specific antibodies. In addition to supplying the cells with oxygen, the concentration of dissolved carbon dioxide also plays a part as a controlled variable.

There are two conventional aeration methods: aerating the headspace of the bioreactor and direct injection of gases through aeration rings. Such devices are known more commonly as "spargers" or "microspargers," depending upon their gas opening pore sizes. Spargers, including drilled hole or open pipe spargers, typically have gas outlet openings of for example 0.8 mm, whereas microspargers, which are generally made from sintered plastics or metals, have pore sizes of for example 15 to 45 µm. Both kinds have specific advantages and drawbacks. The spargers produce larger bubbles, which means that higher gas throughput rates are required to achieve the same "oxygen transfer rate." Spargers, however, can result in bubble-induced cellular toxicity by introducing shear forces on the cells as the bubbles pass through the cell culture. One advantage of spargers, however, is that due to their larger-sized bubbles, they are suitable for stripping or sweeping out $CO_2$. Microspargers were primarily developed to improve gas transfer to cultures by reducing the size of the bubbles introduced into the cell culture. However, microspargers tend to produce foaming as a result of the micro-bubbles interacting with protein in the cell culture, which can result in premature run termination and loss of product. Similar to spargers, microbubbles generated by microspargers also cause shear forces on cells in culture. In particular, these shear forces are generated as a result of the bubbles bursting nearby a cell, which can result in membrane damage and cell death.

The present invention relates in part to the surprising finding that by replacing the sparger or microsparger in the context of a high density cell culture bioreactor with one or more hollow-fiber membrane modules, sustained levels of dissolved oxygen could be achieved at high cell densities without severe effects on culture health during operation. Accordingly, the present invention relates to improved bioprocessing systems and methods for cell culture using the improved bioreactors, e.g., batch-fed or perfusion bioreactor cell culture systems for production of monoclonal or bi-specific antibodies, which are modified to include one or more membrane gas transfer modules in place of a sparger- or microsparger-based aeration system to better regulate the levels of critical gases in a bioreactor cell culture, e.g., the dissolved levels of $O_2$ and $CO_2$, even at high cell densities, without subjecting the cells to shear and bubble-burst associated cell death. Non-limiting aspects and embodiments are provided in the herein Examples and Drawings, as well as the Description below.

Definitions

Unless defined otherwise, all technical and scientific terms used herein have the meaning commonly understood by one of ordinary skill in the art to which this invention belongs. The following references provide one of skill in the art to which this invention pertains with a general definition of many of the terms used in this invention: Singleton et al., Dictionary of Microbiology and Molecular Biology (2d ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2$^{nd}$ Edition, W.B. Saunders Company. For the purposes of the present invention, the following terms are further defined.

As used herein and in the claims, the singular forms "a," "an," and "the" include the singular and the plural reference unless the context clearly indicates otherwise. Thus, for example, a reference to "an agent" includes a single agent and a plurality of such agents.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

The term "obtaining" as in "obtaining the spore associated protein" is intended to include purchasing, synthesizing or otherwise acquiring the spore associated protein (or indicated substance or material).

An "isolated cell" refers to a cell which has been separated from other components and/or cells which naturally accompany the isolated cell in a tissue or mammal.

As used herein, a "sample" refers to a composition that comprises biological materials such as (but not limited to) a bioreactor cell culture sample.

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, can be used. In one embodiment 500 L to 2000 L bioreactors are used. In a preferred embodiment, 1000 L to 2000 L bioreactors are used. For the purposes of this invention, cell culture medium is a media suitable for growth of animal cells, such as mammalian cells, in in vitro cell culture. Cell culture media formulations are well known in the art. Typically, cell culture media are comprised of buffers, salts, carbohydrates, amino acids, vitamins and trace essential elements. "Serum-free" applies to a cell culture medium that does not contain animal sera, such as fetal bovine serum. Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kansas), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

As used herein, the phrase "low-density cell culture" refers to a cell culture having a cell concentration of less than $20 \times 10^6$ cells per ml.

As used herein, the phrase "high-density cell culture" refers to a cell culture having a cell concentration of equal to or more than $20 \times 10^6$ cells per ml. A high-density cell culture includes a cell culture having a cell concentration of about $25 \times 10^6$ cells per ml, about $35 \times 10^6$ cells per ml, about $45 \times 10^6$ cells per ml, about $55 \times 10^6$ cells per ml, about $65 \times 10^6$ cells per ml, about $75 \times 10^6$ cells per ml, about $85 \times 10^6$ cells per ml, about $95 \times 10^6$ cells per ml, about $100 \times 10^6$ cells per ml, about $110 \times 10^6$ cells per ml, about $120 \times 10^6$ cells per ml, about $130 \times 10^6$ cells per ml, about $140 \times 10^6$ cells per ml, about $150 \times 10^6$ cells per ml, about $160 \times 10^6$ cells per ml, about $170 \times 10^6$ cells per ml, about $180 \times 10^6$ cells per ml, about $190 \times 10^6$ cells per ml, about $200 \times 10^6$ cells per ml, about $210 \times 10^6$ cells per ml, about $220 \times 10^6$ cells per ml, about $230 \times 10^6$ cells per ml, about $240 \times 10^6$ cells per ml, about $250 \times 10^6$ cells per ml, about $260 \times 10^6$ cells per ml, about $270 \times 10^6$ cells per ml, about $280 \times 10^6$ cells per ml, about $290 \times 10^6$ cells per ml, and about $300 \times 10^6$ cells per ml.

Bioreactors

The improved bioreactors described herein may be derived from a known bioreactor system, and in particular, bioreactors comprising a sparger or microsparger system for carrying out culture aeration. Bioreactors are commonly used in bioprocessing. As used herein, a "bioreactor" may refer to any manufactured or engineered device or system that supports a biologically active environment. In one case, a bioreactor is a vessel in which a chemical process is carried out which involves organisms or biochemically active substances derived from such organisms. This process can either be aerobic or anaerobic. These bioreactors are commonly cylindrical, ranging in size from liters to cubic meters, and are often made of stainless steel or other materials. A bioreactor may also refer to a device or system meant to grow cells or tissues in the context of cell culture often with the goal of producing a desired biologically-produced product, e.g., a monoclonal or bi-specific antibody. "Bioprocessing" refers to aerobic and anaerobic processes that involve cells in a growth medium, wherein the cells produce (naturally or through genetic engineering) one or more useful biological products or substances, including for example, monoclonal antibodies, bi-specific antibodies, and enzymes. Examples of bioprocesses include yeast fermentation, bacterial fermentation, mammalian cell culture, bacterial culture, and the production of a product using cells, e.g., using mammalian cells such as CHO cells to express a protein, e.g., a therapeutic protein, or an enzyme.

A bioreactor generally includes a vessel in which a bioprocess is carried out, and sensors and process controls that allow parameters of the process to be monitored and controlled. Bioreactors also typically include an agitator, for example a Rushton or marine impeller, that mixes the vessel contents during bioprocessing. It is generally important to carefully control process parameters during bioprocessing, for example gas flow rates, temperature, pH, dissolved oxygen level, and agitation speed and conditions. Dissolved oxygen level is a measure of oxygen transfer from gas to liquid phase, which is important to many bioprocesses and can be difficult to accomplish. While oxygen transfer is generally helped by agitation, agitation speed is often limited by power consumption and in some cases the risk of damage to the microorganisms. In some cases, for example, in the case of mammalian cells, the microorganisms are fragile and may be sensitive to heat, shear, and/or other process conditions.

The bioreactors used herein can be permanent (e.g., stainless steel or glass bioreactors) or disposable (e.g., plastic flask or bag). Examples of reactors suitable for use in the present invention include, but are not limited to stirred tank vessels, airlift vessels and disposable bags that can be mixed by rocking, shaking motion or stirring. Preferably disposable (bio)reactors are used as they are favorable as they require relatively low investment costs, have great operational flexibility, short turn-around times and are easily configurable to the process. Disposable (bio)reactors are commercially available.

The bioreactors that may be used in the present invention may also be selected based on the type of bioprocess that is of interest. For example, mammalian cell bioprocessing typically occurs in three major formats: batch culture, fed-batch culture, and perfusion culture. Batch culture, a discontinuous method where cells are grown in a fixed volume of culture media for a short period of time followed by a full harvest. Cultures grown using the batch method experience an increase in cell density until a maximum cell density is reached, followed by a decline in viable cell density as the media components are consumed and levels of metabolic by-products (such as lactate and ammonia) accumulate. Harvest typically occurs at the point when the maximum cell density is achieved (e.g., typically $5\text{-}10\times10^6$ cells/mL, depending on media formulation, cell line, etc). The batch bioprocess is the simplest culture method, however viable cell density is limited by the nutrient availability and once the cells are at maximum density, the culture declines and production decreases. There is no ability to extend a production phase because the accumulation of waste products and nutrient depletion rapidly lead to culture decline (e.g., typically around 3 to 7 days). Fed-batch culture improves on the batch process by providing bolus or continuous media feeds to replenish those media components that have been consumed. Since fed-batch cultures receive additional nutrients throughout the run, they have the potential to achieve higher cell densities ($>20\times10^6$ cells/ml, depending on media formulation, cell line, etc.) and increased product titers, when compared to the batch method.

Unlike batch processing, a biphasic culture can be created and sustained by manipulating feeding strategies and media formulations to distinguish the period of cell proliferation to achieve a desired cell density (the growth phase) from the period of suspended or slow cell growth (the production phase). As such, fed batch cultures have the potential to achieve higher product titers compared to batch cultures. Typically a batch method is used during the growth phase and a fed-batch method used during the production phase, but a fed-batch feeding strategy can be used throughout the entire process. However, unlike the batch process, bioreactor volume is a limiting factor which limits the amount of feed. Also, as with the batch method, metabolic by-product accumulation will lead to culture decline, which limits the duration of the production phase, about 1.5 to 3 weeks. Fed-batch cultures are discontinuous and harvest typically occurs when metabolic by-product levels or culture viability reach predetermined levels.

Perfusion methods offer potential improvements over the batch and fed-batch methods by adding fresh media and simultaneously removing spent media. Typical large scale commercial cell culture strategies strive to reach high cell densities (greater than $20e10^6$ cells/mL) where almost a third to over one-half of the reactor volume is biomass. With perfusion culture, extreme cell densities of $>1\times10^1$ cells/mL have been achieved and even higher densities are predicted. Typical perfusion cultures begin with a batch culture start-up lasting for a day or two followed by continuous, step-wise and/or intermittent addition of fresh feed media to the culture and simultaneous removal of spend media with the retention of cells and additional high molecular weight compounds such as proteins (based on the filter molecular weight cutoff) throughout the growth and production phases of the culture. Various methods, such as sedimentation, centrifugation, or filtration, can be used to remove spent media, while maintaining cell density. Perfusion flow rates of a fraction of a working volume per day up to many multiple working volumes per day have been reported.

An advantage of the perfusion process is that the production culture can be maintained for longer periods than batch or fed-batch culture methods. However, increased media preparation, use, storage and disposal are necessary to support a long term perfusion culture, particularly those with high cell densities, which also need even more nutrients, and all of this drives the production costs even higher, compared to batch and fed batch methods. In addition, higher cell densities can cause problems during production, such as maintaining dissolved oxygen levels and problems with increased gassing including supplying more oxygen and removing more carbon dioxide, which would result in more foaming and the need for alterations to antifoam strategies; as well as during harvest and downstream processing where the efforts required to remove the excessive cell material can result in loss of product, negating the benefit of increased titer due to increased cell mass.

The present invention relates to improved bioreactors, including any of the types of bioreactors indicated above, wherein the sparger/microsparger is replaced with one or more membrane gas transfer modules described herein. The present invention relates in part to the surprising finding that by replacing the sparger or microsparger in the context of a high density cell culture bioreactor with one or more hollow-fiber membrane modules, either within the bioreactor itself or exterior thereto, sustained levels of dissolved oxygen could be achieved at high cell densities without severe effects on culture health during operation. Accordingly, the present invention relates to improved bioprocessing systems and methods for cell culture using the improved bioreactors, e.g., batch-fed or perfusion bioreactor cell culture systems for production of monoclonal or bi-specific antibodies, which are modified to include one or more membrane gas transfer modules in place of a sparger- or microsparger-based aeration system to better regulate the levels of critical gases in a bioreactor cell culture, e.g., the dissolved levels of $O_2$ and $CO_2$, even at high cell densities, without subjecting the cells to bubble-burst associated cell death.

In general, the bioreactors of the invention may include a vessel in which a bioprocess takes place. A vessel, for example vessel 101 of FIG. 1A, or 302 of FIG. 1B, is generally of an autoclavable, inert material such as glass, plastic, or stainless steel, and may or may not be jacketed. In some cases, the vessel may be relatively low volume, e.g., less than about 0.5 L, or 1 L, or 2 L, or 4 L, or 10 L, or 20 L, or 40 L, or 100 L. In other cases, the vessel may be relatively high volume, e.g., greater than 100 L, or 200 L, or 300 L, or 500 L, or 1000 L, or 5,000 L, or 10,000 L, or 30,000 L. Suitable low volume vessels may have a total capacity, for example, of from about 0.5 L to 5 L, e.g., 0.5 L, 1 L, 2 L, 4 L, 10 L, 20 L, 40 L, or 50 L. For example, the total capacity of the vessel may be 75 L, 150 L, 300 L, 500 L, 1000 L, 1500 L, 3000 L, or 5000 L. It may be preferred that the vessel have an aspect ratio (diameter:height) of, for example, about 0.5:1 to about 4:1, or about 0.5:1 to 2:1, e.g., about 0.5:1 to 1:1. The invention contemplates the use of any suitable bioreactor volume or aspect ratio and it not limited to those indicated above.

A shaft (e.g., shaft 104 of FIG. 1A) extends into the vessel, and an impeller (e.g., impeller 104 of FIG. 1A) is mounted at the distal end of the shaft. As will be discussed in detail below, the impeller creates a circulating flow in the liquid (e.g., cell culture media) in the vessel, as indicated by the arrows surrounding the impeller. In general, the shaft would be driven by a motor.

The bioreactor may include any other desired bioreactor components and features including pumps, container for replacement growth media, containers for nutrients, a collection or harvesting module (e.g., harvesting module 313 of FIG. 1B), and a source of gas or multiple gas sources and appropriate valving, tubing, and mixing devices. The bioreactors contemplated herein can also include dissolved oxygen probes, dissolved carbon dioxide probes, pH probes, and redox (ORP) probes (see FIGS. 1C and 1D) for monitoring these parameters, and a sampling probe for sampling or harvesting the vessel contents. A condenser can also be provided for condensation of volatiles.

The bioreactor contemplated herein generally include a controller that is configured to control the process parameters by receiving signals from various monitoring devices (e.g., the probes shown in FIGS. 1C and 1D) and adjusting the process parameters based on this data. The controller may be, for example, a programmable logic controller (PLC) with an operator interface. The controller may optionally be configured to control multiple vessels.

In some implementations, gas delivery is through the shaft of the impeller. For example, the shaft may include a bore through which gas is delivered, and one or more orifices through which gas exits into the vessel.

The bioreactors contemplated herein may also include a number of other features to enhance bioprocessing. For example, the vessel may be cooled (or heated), e.g., with a water jacket or other cooling/heating system, to maintain a desired process temperature. The vessel may also be heated with any suitable heating system, including those that are configured exterior to the growth vessel or those placed within the growth vessel. A foam detector may be provided, and an anti-foam delivery system may be included to deliver an anti-foam agent to the vessel should excessive foaming occur. In some implementations, the bioreactor is sterilizable in place, e.g., with an automatic steam injection system. Various access ports may be provided in the vessel.

The bioreactors contemplated herein may also include one or more membrane gas transfer modules, which can be located within the bioreactor vessel, or located externally to the vessel but in communication with a flow path of cell culture media. For example, flow path 314 of FIG. 1B provides a two-module system (309a and 309b) for gas exchange. An embodiment is shown in and FIG. 1B.

FIG. 1B shows a schematic of an embodiment of the bioreactors disclosed herein. In this embodiment, an improved bioreactor 300 includes one or more exterior-located membrane gas transfer modules 309 which are fed cell culture along a flow path 314 from/to the bioreactor in series by a pump 312. The first membrane gas transfer module 309b has a gas input 310b and gas exhaust 311b. The second membrane gas transfer module 309a also has a gas input 310a and a gas exhaust 311a. The pump 312 moves the cell culture from the bioreactor 300 along the flow path 314 (i.e., recirculation loop) through the first membrane gas transfer module 309b and then through the second membrane gas transfer module 309a, allowing the cell culture to interact with the gasses flowing through the membrane modules, which are introduced at the gas inlets and which exit out the exhaust ports. The gases interact with the cell culture by passages through the gas-permeable membranes in the modules that separate the gas flow zone from the cell culture flow path. The modules allow the addition of certain gasses (e.g., oxygen) and/or removal of other gasses (e.g., $CO_2$) from the bioreactor cell culture without the generation of bubbles. The cell culture, once treated by the modules along flow path 314, is return to the bioreactor 300. The exact configuration shown in FIG. 1B is not intended to limit other possible configurations contemplated herein. A computer controller can be included to modulate $O_2$ and $CO_2$ gas flow to the membranes to maintain dissolved $O_2$ and $CO_2$ at preferred concentrations in the bioreactor.

During operation, temperature may also be an important factor in maintaining cell culture health. The temperature will depend on the nature of the culture and product being expressed, as different biological materials perform optimally at different temperatures. The temperature may vary slightly during operation of the bioreactor. The temperature may be between about −5 and 120° C., or between −5 and 0° C., or between about 0 and 100° C., or between about 0 and 50° C., or between about 0 and 20° C., or between about 20 and 120° C., or between about 50 and 120° C., or between about 90 and 120° C., or between about 10 and 45° C., or between about 10 and 35° C., or between about 10 and 25° C., or between about 20 and 55° C., or between about 30 and 55° C., or between about 40 and 55° C., or between about 15 and 45° C., or between about 17 and 42° C., or between about 20 and 40° C., or between about 20 and 30° C., or between about 30 and 40° C., and may be about −5°, 0°, 5°, 10°, 15°, 17°, 20°, 25°, 28°, 30°, 35° 37°, 40°, 42° 45° 50°, 60°, 70°, 80°, 90°, 100°, 110° or 120° C.

The cells of the bioreactor may be grown to a suitable cell density. As used herein, "cell density" refers to the number of cells in a given volume of culture medium. "Viable cell density" refers to the number of live cells in a given volume of culture medium, as determined by standard viability assays (such as, for example, the trypan blue dye exclusion method). The trypan blue dye exclusion test is used to determine the number of viable cells present in a cell suspension. It is based on the principle that live cells possess intact cell membranes that exclude certain dyes, such as trypan blue, whereas dead cells do not. In this test, A cell suspension is simply mixed with dye and then visually examined (or automated imaging-based equipment) to determine whether cells take up or exclude dye."

The desired viable cell density at the transition between the growth and production phases and maintained during the production phase is one that provides a packed cell volume of equal to or less than 35%. In one embodiment, the viable cell density is at least about $10 \times 10^6$ viable cells/mL. In other embodiments, that viable cell density can reach $20 \times 10^6$, $30 \times 10^6$, $40 \times 10^6$, $50 \times 10^6$, $60 \times 10^6$, $70 \times 10^6$, $80 \times 10^6$, $90 \times 10^6$, $100 \times 10^6$, $110 \times 10^6$, $120 \times 10^6$, $130 \times 10^6$, $140 \times 10^6$, $150 \times 10^6$, $160 \times 10^6$, $170 \times 10^6$, $180 \times 10^6$, $190 \times 10^6$, $200 \times 10^6$, $210 \times 10^6$, $220 \times 10^6$, $230 \times 10^6$, $240 \times 10^6$, or $250 \times 10^6$ viable cells/mL. In one embodiment the viable cell density is at least about $10 \times 10^6$ viable cells/mL to $70 \times 10^6$ viable cells/mL In one embodiment the viable cell density is at least about $10 \times 10^6$ viable cells/mL to $60 \times 10^6$ viable cells/mL. In one embodiment the viable cell density is at least about $10 \times 10^6$ viable cells/mL to $50 \times 10^6$ viable cells/mL. In one embodiment the viable cell density is at least about $10 \times 10^6$ viable cells/mL to $40 \times 10^6$ viable cells/mL. In a preferred embodiment the viable cell density is at least about $10 \times 10^6$ viable cells/mL to $30 \times 10^6$ viable cells/mL. In another preferred embodiment the viable cell density is at least about $10 \times 10^6$ viable cells/mL to $20 \times 10^6$ viable cells/mL. In another preferred embodiment, the viable cell density is at least about $20\times10^6$ viable cells/mL to $30\times10^6$ viable cells/mL In another preferred embodiment the viable cell density is at least about $20\times10^6$ viable cells/mL to at least about $25\times10^6$ viable cells/mL, more preferably at least about $20\times10^6$ viable cells/mL. In still another embodiment, the viable cell density is at least about $20\times10^6$ to $120\times10^6$ viable cells/mL, or at least about $40\times10^6$ to $140\times10^6$ viable cells/mL, or at least about $60\times10^6$ to $160\times10^6$ viable cells/mL, or at least about $80\times10^6$ to $180\times10^6$ viable cells/mL, or at least about $100\times10^6$ to $200\times10^6$ viable cells/ml, Membrane Modules The present invention relates to a bioreactor comprising one or more membrane gas transfer modules to regulate, control, or otherwise carry out the gas exchange process involved or required during the operation of a bioreactor, e.g., a perfusion or batch-fed bioreactor. Preferably, the bioreactors do not introduce bubbles into cell media as a result of the membrane-based mass transfer processes. The bioreactors are suitable for growth of high density cultures, such as those having a cell density of at least about $20\times10^6$ to $120\times10^6$ viable cells/mL, or at least about $40\times10^6$ to $140\times10^6$ viable cells/mL, or at least about $60\times10^6$ to $160\times10^6$ viable cells/mL, or at least about $80\times10^6$ to $180\times10^6$ viable cells/mL, or at least about $100\times10^6$ to $200\times10^6$ viable cells/mL, The gas exchange processes include the addition of gases to the cell culture (e.g., addition of $O_2$) and removal of gases from the cell culture (e.g., $CO_2$ stripping), preferably without the introduction of bubbles into the culture media.

In addition, the present invention relates to a method of high-density cell culture comprising the use of one or more membrane gas transfer modules to regulate, control, or otherwise carry out the gas exchange processes involved or required during the operation of the high-density cell culture bioreactor, e.g., a perfusion or batch-fed bioreactor. Preferably, the bioreactors do not introduce bubbles into cell media as a result of the membrane-based mass transfer processes. The cell culture method is suitable for growing high density cultures, such as those having a cell density of at least about $20\times10^6$ to $120\times10^6$ viable cells/mL, or at least about $40\times10^6$ to $140\times10^6$ viable cells/mL, or at least about $60\times10^6$ to $160\times10^6$ viable cells/mL, or at least about $80\times10^6$ to $180\times10^6$ viable cells/mL, or at least about $100\times10^6$ to $200\times10^6$ viable cells/mL. The gas exchange processes include the addition of gases to the cell culture (e.g., addition of $O_2$) and removal of gases from the cell culture (e.g., $CO_2$ stripping), preferably without the introduction of bubbles into the culture media.

Figure 1E:
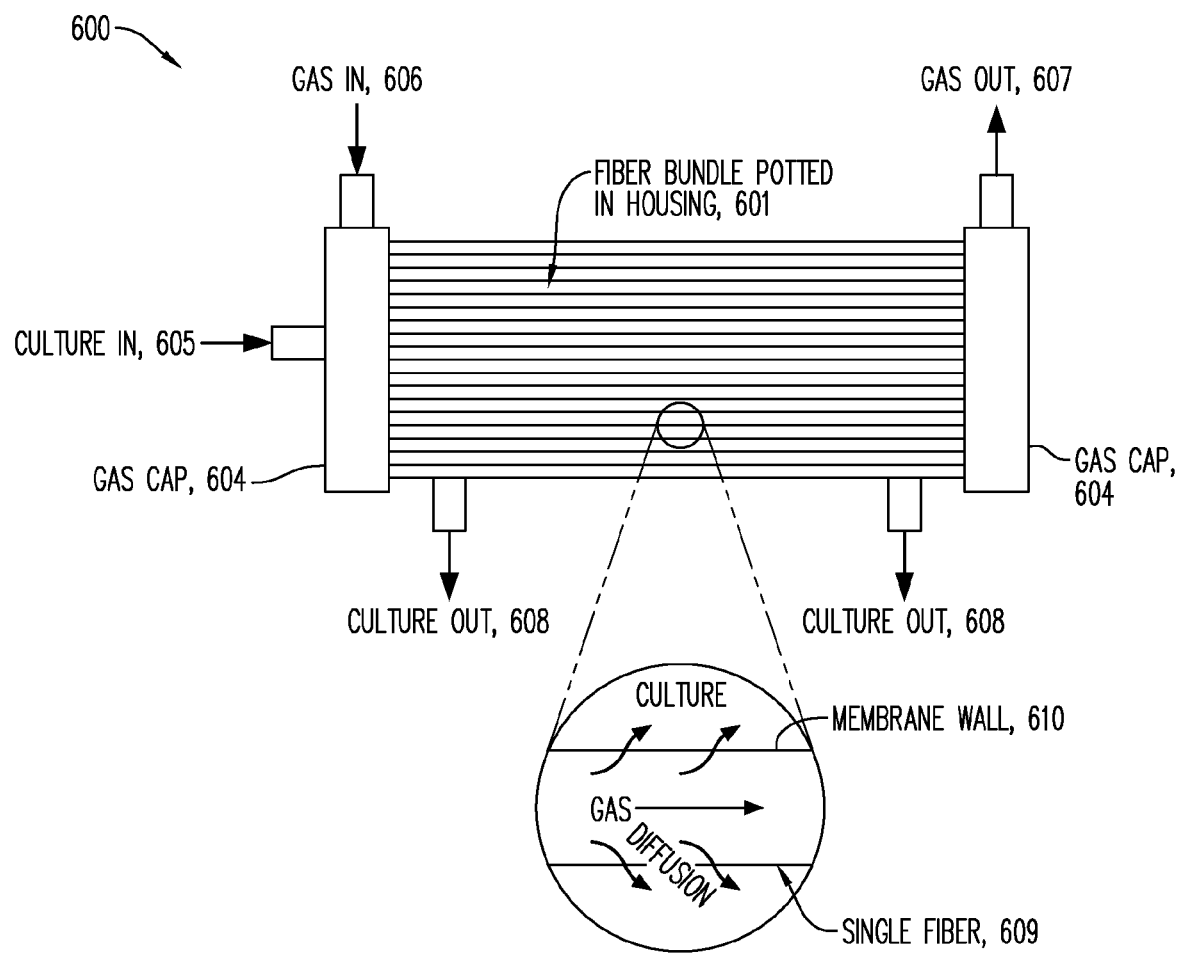
FIG. 1E shows a generalized schematic of a membrane gas transfer module 600 that may be used in connection with the improved bioreactors of the invention. As a matter of general, but non-limiting construction, the membrane module may include a hollow fiber bundle 601 of gas-permeable hollow fiber tubes 609 which are held together with a potting or seal 603 (not shown), and then encased within a housing or shell 605 (not shown) and fitted with inlet caps 604 at each end to allow introduction of a flow of one or more gasses through the interior of each hollow fiber. The housing also may including one or more inlet/outlet ports (605, 608) for a flow path of cell culture that enters in one port, flows through the housing in the spaces surrounding the hollow fibers, and then exists out the outlet port. The housing also may include one or more inlet/outlet ports (606, 607) for a flow of one or more gasses through the interior lumen of each of the gas-permeable hollow fiber tubes. In practice, a flow path of cell culture is pumped into an inlet 605 on the housing and flows through the housing through the exterior space around each hollow fiber of the hollow fiber bundle, and exits through the outlet ports 608. While inside the housing, the cell culture in in contact with the gas-permeable membranes of the hollow fiber bundle, which carry the flow of the one or more gasses in the luminal space. In use, a "feed" mixture of gasses may enter through an inlet port and flows into the inside of the hollow fibers 609. The gasses transfer from the inside of the hollow fibers, through the gas-permeable membrane wall 610, into the cell culture flow path (which resides external to the hollow fibers). The gasses that pass through the membranes are the "permeate," and the gasses that remain inside the hollow fibers is the "retentate."

As used herein, the term "membrane gas transfer module" refers to a device comprising a sealed housing having a first inlet and a first outlet and defining a first flow path, and at least one membrane contained within the housing connected to at least a second inlet and second outlet and defining a second flow path, and wherein the first flow path and the second flow path are separated by the membrane. An exemplary membrane gas transfer module is depicted in FIG. 1E, which shows a generalized schematic of a membrane gas transfer module 600 that may be used in connection with the improved bioreactors of the invention. As a matter of general, but non-limiting construction, the membrane module may include a hollow fiber bundle 601 of gas-permeable hollow fiber tubes 602 which are held together with a potting or seal 603, and then encased within a housing or shell 605 and fitted with inlet caps 604 at each end to allow introduction of a flow of one or more gasses through the interior of each hollow fiber. The housing also may including one or more inlet/outlet ports (606, 607) for a flow path of cell culture that enters in one port, flows through the housing in the spaces surrounding the hollow fibers, and then exists out the outlet port. In practice, a flow path of cell culture is pumped into one inlet on the housing and flows through the housing around in exterior space around each hollow fiber of the hollow fiber bundle, and exits through the outlet port. While inside the housing, the cell culture is in contact with the exterior of the gas-permeable membranes of the hollow fiber bundle.

In one embodiment, membrane modules may comprise a first flow path, which may be for cell culture medium, which enters a first inlet traversing the first flow path and exits a first outlet. The membrane modules may comprise a second flow path for one or more gasses or gas mixtures. The gasses would enter a second inlet, traverse the second flow path, and then exit a second outlet. During the time the gasses are traversing the second flow path, the gasses may permeate from the second flow path through the membrane into the cell culture in the first flow path. In addition, dissolved gasses in the cell culture of the first flow path may permeate the membrane thereby passing into the second flow path. The outlet of the second flow path can also be referred to as the gas "exhaust" port.

Figure 2:
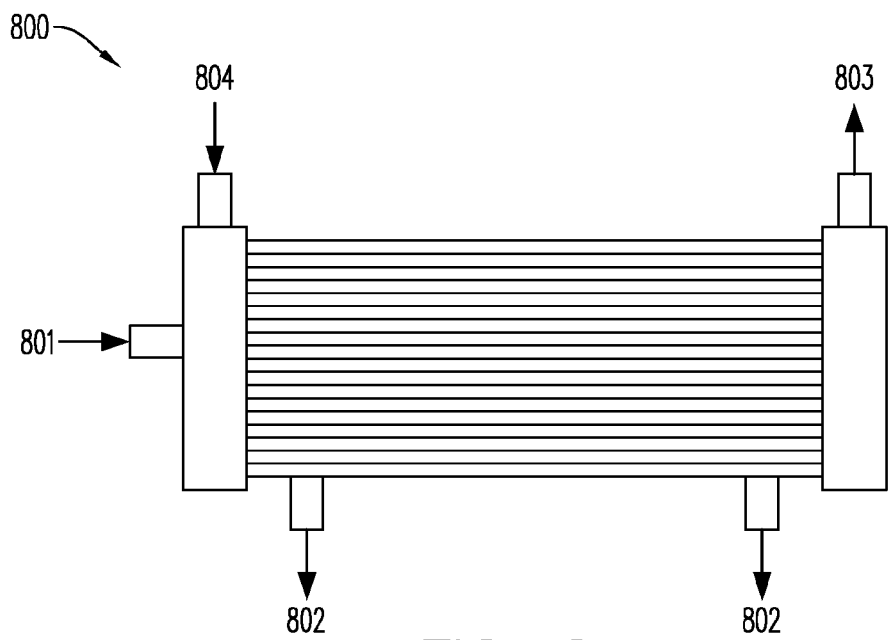
FIG. 2 shows an embodiment of a membrane gas transfer module 800 that may be used in connection with the improved bioreactors described herein. The module includes a "shell side in" inlet 801 for receiving cell culture media, which then traverses throughout the housing or shell in the spaces surrounding each of the hollow fibers of the hollow fiber bundle. The culture media eventually exits the housing through the "shell side out" outlet ports 802. In this example, there are two outlet ports; however, any number of outlet ports could be used. The module also includes one or more "tube (lumen) side in" inlet ports 804 for receiving one or more gasses or a gas mixture, and which enters into the lumen or interior space of each of the hollow fibers of the hollow fiber bundle. The gasses then traverse the length of the hollow fibers and exit out of the one or more "tube (lumen) side out" outlet ports 803. This configuration establishes both a "gas flow zone," which is in the interior space of lumen of the hollow fibers, and a "media or cell culture flow zone," which is the space confined to within the shell or house but exterior to the hollow fibers. Gasses in the gas flow zone may permeate the membrane, thereby transferring into the media flow zone. Alternately, dissolved gasses (e.g., $CO_2$) may permeate the hollow fiber membranes, thereby transferring into the gas flow zone, and exiting the module as "exhaust" through the gas outlet port.

FIG. 2 shows another embodiment of the flow paths of a membrane module used herein. The figure shows an embodiment of a membrane gas transfer module 800 that may be used in connection with the improved bioreactors described herein. The module includes a "shell side in" inlet 801 for receiving cell culture media, which then traverses throughout the housing or shell in the spaces surrounding each of the hollow fibers of the hollow fiber bundle. The culture media eventually exits the housing through the "shell side out" outlet ports 802. In this example, there are two outlet ports; however, any number of outlet ports could be used. The module also includes one or more "tube (lumen) side in" inlet ports 804 for receiving one or more gasses or a gas mixture, and which enters into the lumen or interior space of each of the hollow fibers of the hollow fiber bundle. The gasses then traverse the length of the hollow fibers and exit out of the one or more "tube (lumen) side out" outlet ports 803. This configuration establishes both a "gas flow zone," which is in the interior space of lumen of the hollow fibers, and a "media or cell culture flow zone," which is the space confined to within the shell or house but exterior to the hollow fibers. Gasses in the gas flow zone may permeate the membrane, thereby transferring into the media flow zone. Alternately, dissolved gasses (e.g., $CO_2$) may permeate the hollow fiber membranes, thereby transferring into the gas flow zone, and exiting the module as "exhaust" through the gas outlet port.

Figure 3:
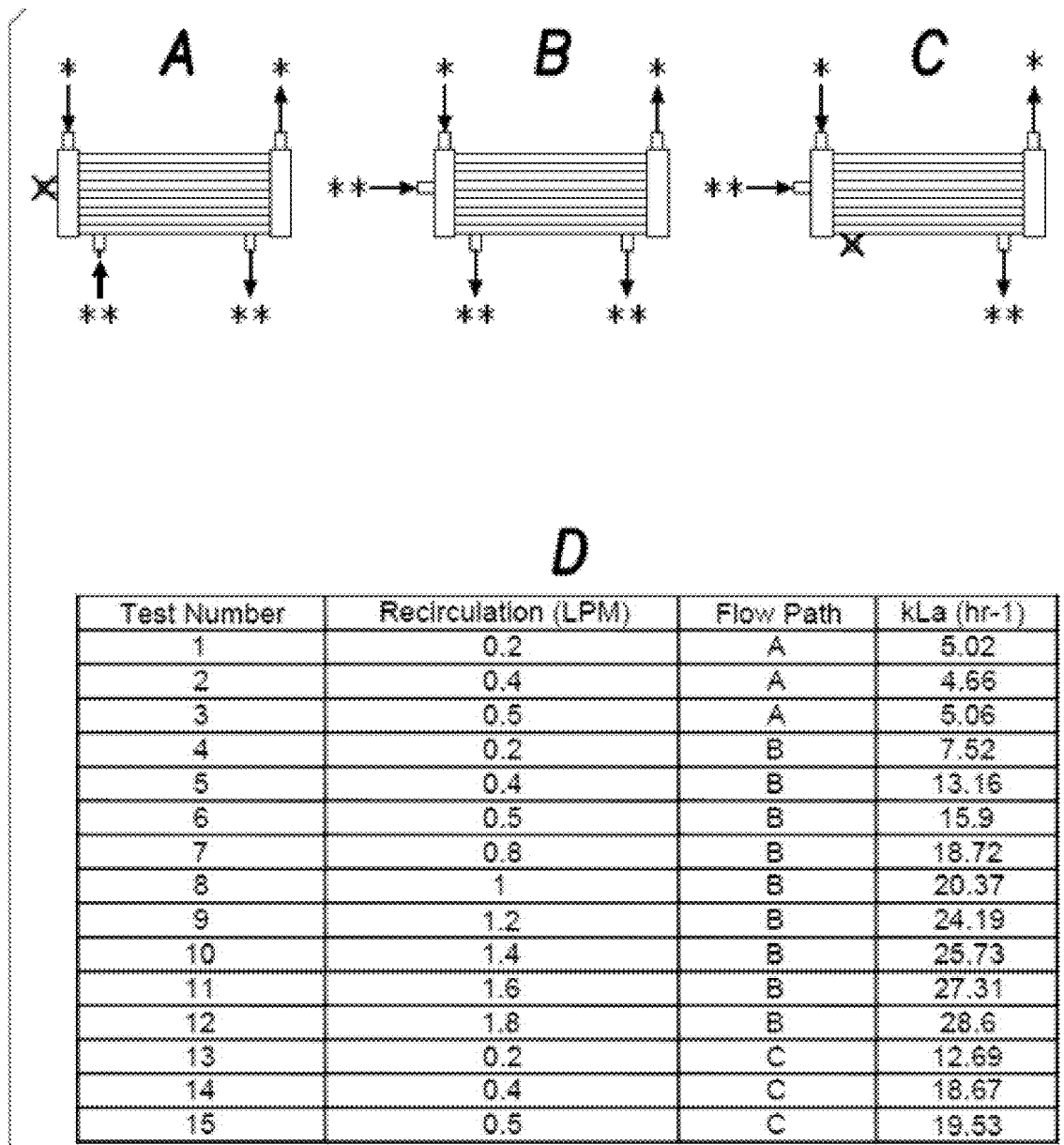
FIGS. 3A, 3B, and 3C show various configuration of flow path of gas (arrows marked with "*") and cell culture media (arrows marked with "**") in a typical membrane gas transfer module. The ports marked with an "x" are blocked. Gas transfer efficiency is highest in configuration FIG. 3C as compared to the configurations of FIG. 3A and FIG. 3B given the same flow rates. The table shown in FIG. 3D provides example kLa (liquid phase mass transfer coefficient) measured for transfer of oxygen through a membrane gas transfer module with 2500 $cm^2$ surface area for gas transfer. Restrictions in flow path FIG. 3A and FIG. 3C prevent the ability to achieve flow greater than 0.5 LPM (liter per minute). Alternate membrane sizes can be used for different kLa to support larger and smaller bioreactors.

FIG. 3 also provides exemplary forms of the flow paths used for the gas transfer modules. In particular, the figures show various configuration of flow path of gas (arrows marked with "*") and cell culture media (arrows marked with "**") in a typical membrane gas transfer module in configurations A, B, and C. The ports marked with an "x" are blocked. As used herein, the term "membrane" refers to a layer of material that allows one substance (e.g., a gas) to pass through it while blocking another (e.g., a liquid). This selectivity may be based on particle size, phase of material (liquid vs. gas), or solubility. Additionally, the separation occurs in the presence of a driving force, such as a difference in pressure, temperature or concentration between one side of the membrane and the other. Membranes include "dense or non-porous membranes" and "porous membranes."

As use herein, the term "dense membrane" or "nonporous membrane" refers to a solid material, without pores or voids. Examples include polymers (such as silicone or polydimethylsiloxane (PDMS)), metals (such as palladium), and ceramics. Dense membranes allow substances to pass through them by a process of solution and diffusion, in which the substance dissolves into the membrane and passes through it to the other side. For examples, silicone can form a dense membrane. Because silicone is dense (and not porous) liquids cannot grossly transfer through the membrane, enabling its use in liquid contacting applications with all compatible liquids regardless of surface tension. Moreover, the dense membrane also provides a means for separating gases due to the permeability difference between gases in silicone.

As used herein, the term a "porous membrane" is an otherwise solid material with pores, or holes, of a particular size or range of sizes. These membranes separate on the basis of size exclusion: substances larger than the pores do not pass through, while those smaller than the pores do.

As used herein, the term "asymmetric membrane" is comprised of a single material, often porous, that has differing characteristics (such as pore size) from one side to the other. This feature allows "tighter" selectivity to occur at the surface and less restriction as a material passes through the membrane matrix.

As used herein, the term "composite membrane" is made up of more than one material, often a thin selective layer of a dense material applied to a porous support layer.

As used herein, the term "permeability coefficient" in relation to a membrane is a parameter defined as the transport flux of a gas (rate of gas permeation per unit area), per unit transmembrane driving force, per unit membrane thickness.

In various embodiments, the membrane gas transfer modules comprise one or more silicone membranes. Silicone, also known as polydimethylsiloxane (PDMS), is among the most gas permeable dense polymeric membrane materials available. Gases permeate silicone by a solution/diffusion mechanism, whereby the rate of gas permeation is directly proportional to the product of solubility of the gas, and the rate of diffusion of the dissolved gas in silicone. The permeability coefficient is a parameter defined as the transport flux of a gas (rate of gas permeation per unit area), per unit transmembrane driving force, per unit membrane thickness. The permeability coefficient for various gases and vapors in silicone is presented in the table below.

TABLE 1

Silicone permeability coefficient for various exemplary gases

| Gas | Silicone permeability cooefficient (Barrer*) |
|---|---|
| Nitrogen | 280 |
| Oxygen | 600 |
| Hydrogen | 650 |
| Methane | 950 |
| Carbon monoxide | 340 |
| Carbon dioxide | 3250 |

*1 Barrer = $10^{-10}$ cm$^3$ (STP) · cm/cm$^2$ · s · cm-Hg. Unless otherwise noted, permeabilities are measured and reported at 25 C. (RTP) and not (STP) From: THIN SILICONE MEMBRANES-THEIR PERMEATION PROPERTIES AND SOME APPLICATIONS, Annals of the New York Academy of Sciences, vol. 146, issue 1 Materials in, pp. 119-137 W. L. Robb It will be appreciated that the rate of gas transfer across the membrane is proportional to the gas permeability coefficient, the membrane surface area, the trans-membrane gas partial pressure difference, and inversely proportional to the membrane thickness. Thus gas transfer across a membrane increases with increased gas permeability coefficient, increased surface area, increased transmembrane gas partial pressure and decreased membrane thickness.

In certain embodiments, the membranes used herein may be porous, e.g., nanoporous, mesoporous or microporous, or it may have a combination of nanoscale and/or mesoscale and/or microscale pores. The porosity of the nanoporous solid or gel may be between about 40 and 90%, or between about 40 and 75% or between about 40 and 60% or between about 50 and 90% or between about 60 and 90% or between about 70 and 90% or between about 50 and 80% or between about 60 and 70%, and may be about 40, 45, 50, 55, 60, 65, 70, 75, 80, 85 or 90%. The pores may have a mean diameter between about 1 nm and 10 microns, or between about 1 nm and 1 micron or between about 1 and 500 nm or between about 1 and 100 nm or between about 1 and 50 nm or between about 1 and 10 nm or between about 100 nm and 10 microns or between about 500 nm and 10 microns or between about 1 and 10 microns or between about 10 nm and 1 micron or between about 50 and 500 nm or between about 100 and 200 nm, and may have a mean diameter about 1, 5, 10, 15, 20, 25, 30, 35, 40, 45, 50, 75, 100, 150, 200, 250, 300, 350, 400, 450, 500, 600, 700, 800 or 900 nm or about 1, 2, 34, 5, 6, 7, 8, 9 or 10 microns.

The thickness of the membranes used herein may be any suitable thickness. In various embodiments, the thickness may be between about 0.1 and 10 mm thick, and may be between about 0.1 and 5 mm thick or between about 0.1 and 2 mm thick or between about 0.1 and 1 mm thick or between about 1 and 10 mm thick or between about 5 and 1.0 mm thick or between about 0.5 and 5 mm thick or between about 1 and 5 mm thick or between about 1 and 2 mm thick, and may be about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9 or 10 mm thick. When the membrane is fabricated, the distribution of cells within the nanoporous material may be approximately homogeneous or they may be heterogenous. In addition, the membranes may contain a mixture of pores having different sizes.

In one embodiment, the bioreactors of the invention may be configured as a hollow-fiber gas transfer module, e.g., a PERMSELECT® silicone hollow fiber membrane module or a module having similar or equivalent properties. Hollow fibers constitute a self-supported, inherently stable membrane structure that can tolerate high pressure differences between the inside and outside of the hollow fiber membrane. Hollow fiber membranes are typically packaged in membrane modules in which thousands of hollow fibers are bundled in a very compact volume and sealed or potted within a housing as shown in the figure below. Exemplary hollow-fiber modules are shown in FIG. 1E and FIG. 2. Consequently, the sum of the surface area of each individual hollow fiber membrane constitutes the total membrane area for the module, and it becomes apparent how it is possible to achieve high membrane surface densities with hollow fiber membranes.

Membrane modules will typically have an inlet and an outlet port in fluid communication with the inside of all the hollow fibers (also known as tube side) which are manifolded at both ends of the fiber bundle. For example, see FIG. 1E. Similarly the membrane modules will have one or more ports in fluid communication to the outside of the hollow fibers or the shell side. In operation, as exemplified in FIG. 2, the side of the hollow fiber membranes (shell or tube) in which a gas or liquid should flow will depend on the specific application for the membrane module, and is selected to maximize membrane module performance. For example, as shown in FIG. 2, in membrane gas separation a feed mixture of gases enters the membrane module through the inlet port to the tube side and flows through the inside of the hollow fiber membranes. The gas species in the mixture with higher permeability will transfer at a greater rate across the walls of hollow fiber membranes leaving behind the less permeable species. The transferred gas is referred to as the permeate. In the shell side, a vacuum can be applied or a sweep gas (or liquid) can flow therein to carry away the permeate. Exiting the outlet of the tube side is the retentate which constitutes a gas mixture with a higher concentration of the less permeable gas species.

In various embodiments, the modules can be used in the adding and/or removing of dissolved gases to/from liquids. In operation, a liquid stream flows on one side of the membrane and a mixture of gases flows on (or vacuum is applied to) the other side of the membrane. Each gas species flows from the side of the membrane with higher partial pressure to the side with lower partial pressure, thereby tending to equilibrate both sides. Thus it is possible to control the dissolved gases in a liquid stream flowing through the module by controlling the gas mixture (or vacuum) applied. This principle can be used to regulate the levels of dissolved oxygen and carbon dioxide in the cell culture.

Cells

The improved bioreactors described herein can be used in microbial fermentation and/or cell culture bioprocesses utilizing various microorganisms and cell types. Cells which can be used are in principle all cells known to the person skilled in the art, which have the ability to produce a biological product. The cells may be eukaryotic, for example, filamentous fungi, for example *Aspergillus niger, Aspergillus oryzae, Trichoderma reesei, Penicilliumi chrysogenum*, yeasts, for example *Saccharomyces cerevisiae, Kluyveromyces lactis, Phaffia rhodozyma*, yeast from the genus *Pichia*, for example *Pichia pastoris* or prokaryotic, for instance *Escherichia coli, Bacillus* sp., for example *B. licheniformis, B. subtilis, B. amyloliquefaciens, B. aikalophilus, Streptomyces* sp., *Corynebacterium glutamicum, Pseudomonas* sp. Examples of eukaryotic cells are for example also described in Chu, L., Robinson, D. K., (2001) Curr. Opinion Biotechn., vol. 12, p. 180-187. Preferably, the cells that are used in the process of the present invention are animal cells, in particular mammalian cells. Examples of mammalian cells include CHO (Chinese Hamster Ovary) cells, hybridomas, BHK (Baby Hamster Kidney) cells, myeloma cells, human cells, for example HEK-293 cells, human lymphoblastoid cells, E1 immortalized HER cells, mouse cells, for example NS0 cells.

Examples of cell types for culture and harvesting, using the bioreactor of this invention include but are not limited to monoclonal antibody-secreting hybridoma cells derived from mice, rats, rabbit or human, Eukaryotic cells, biochemical markers, recombinant peptides or nucleotide sequences of interest, proteins, yeast, insect cells, stable or viral infected, avian cells or mammalian cells such as CHO cells, monkey cells, lytic products and the like for medical, research or commercial purposes.

Media

The improved bioreactors described herein may be used on conjunction with any suitable cell culture or microbial growth media. Methods for choosing and optimizing appropriate cell culture media or microbial media are well-known to those having ordinary skill in the art and can vary depending upon a great deal of factors, including, the type of bioprocessor (e.g., fed-batch, perfusion, continuous-flow), the type of cell lines or microbial cells used, and the particular biological product attempting to be expressed.

An important step in cell culture is selecting an appropriate growth medium for in vitro cultivation. A growth medium or culture medium is a liquid or gel designed to support the growth of microorganisms, cells, or small plants. Cell culture media generally comprise an appropriate source of energy and compounds which regulate the cell cycle. A typical culture medium is composed of a complement of amino acids, vitamins, inorganic salts, glucose, and serum as a source of growth factors, hormones, and attachment factors. In addition to nutrients, the medium also helps maintain pH and osmolality.

Bioprocessing is generally conducted in an aqueous growth medium, which can contain a nitrogen source or other nutrient source, e.g., urea, along with vitamins and trace minerals and metals. It is generally preferable that the growth medium be sterile, or at least have a low microbial load, e.g., bacterial count. Sterilization of the growth medium may be accomplished in any desired manner. However, in preferred implementations, sterilization is accomplished by irradiating the growth medium or the individual components of the growth medium prior to mixing. The dosage of radiation is generally as low as possible while still obtaining adequate results, in order to minimize energy consumption and resulting cost.

Animal cells can be cultured either using a completely natural medium or an artificial/synthetic medium along with some natural products. Natural media consist solely of naturally occurring biological fluids. Natural media are very useful and convenient for a wide range of animal cell culture. The major disadvantage of natural media is its poor reproducibility due to lack of knowledge of the exact composition of these natural media. Artificial or synthetic media are prepared by adding nutrients (both organic and inorganic), vitamins, salts, $O_2$ and $CO_2$ gas phases, serum proteins, carbohydrates, cofactors. Different artificial media have been devised to serve one or more of the following purposes: 1) immediate survival (a balanced salt solution, with specific pH and osmotic pressure); 2) prolonged survival (a balanced salt solution supplemented with various formulation of organic compounds and/or serum); 3) indefinite growth; 4) specialized functions.

Artificial media are generally grouped into four categories: (1) serum-containing media; (2) serum-free media; (3) chemically-defined media; and (4) protein-free media.

In serum-containing media, fetal bovine serum is the most common supplement in animal cell culture media. It is used as a low-cost supplement to provide an optimal culture medium. Serum provides carriers or chelators for labile or water-insoluble nutrients, hormones and growth factors, protease inhibitors, and binds and neutralizes toxic moieties.

With serum-free media, the presence of serum in the media can be associated with many drawbacks and can lead to serious misinterpretations in immunological studies. A number of serum-free media have been developed. These media are generally specifically formulated to support the culture of a single cell type, such as Knockout Serum Replacement and Knockout DMEM from Thermo Fisher Scientific for stem cells, and incorporate defined quantities of purified growth factors, lipoproteins, and other proteins, which are otherwise usually provided by the serum. These media are also referred to as 'defined culture media' since the components in these media are known.

In chemically-defined media, these media contain contamination-free ultra-pure inorganic and organic ingredients, and may also contain pure protein additives, like growth factors. Their constituents are produced in bacteria or yeast by genetic engineering with the addition of vitamins, cholesterol, specific amino acids, and fatty acids.

With protein-free media, there is an absence of protein. Compared to serum-supplemented media, use of protein-free media can in some instances promote superior cell growth and protein expression and facilitates downstream purification of any expressed product. Formulations like MEM, RPMI-1640 are protein-free and protein supplement is provided when required.

It will also be appreciated that culture media contain a mixture of amino acids, glucose, salts, vitamins, and other nutrients, and available either as a powder or as a liquid form from commercial suppliers. The requirements for these components vary among cell lines, and these differences are partly responsible for the extensive number of medium formulations. Each component performs a specific function, including:

Buffering systems: regulating pH is critical for optimum culture conditions and is generally achieved by using natural buffering systems or chemical buffering systems. In a natural buffering system, gaseous $CO_2$ balances with the $CO_3/HCO_3$ content of the culture medium. Cultures with a natural buffering system need to be maintained in an air atmosphere with 5-10% $CO_2$, usually maintained by an $CO_2$ incubator. Natural buffering system is low cost and non-toxic.

Chemical buffering systems are also used. Chemical buffering using a zwitterion, HEPES, has a superior buffering capacity in the pH range 7.2-7.4 and does not require a controlled gaseous atmosphere. HEPES is relatively expensive and toxic at a higher concentration for some cell types. HEPES has also been shown to greatly increase the sensitivity of media to phototoxic effects induced by exposure to fluorescent light.

Cell culture may also include pH indicators, such as phenol red. Most of the commercially available culture media include phenol red as a pH indicator, which allows constant monitoring of pH. During the cell growth, the medium changes color as pH is changed due to the metabolites released by the cells. At low pH levels, phenol red turns the medium yellow, while at higher pH levels it turns the medium purple. Medium is bright red for pH 7.4, the optimum pH value for cell culture.

The cell culture media used herein may also contain inorganic salts. Inorganic salt in the media help to retain the osmotic balance and help in regulating membrane potential by providing sodium, potassium, and calcium ions. Culture may also benefit from the presence of amino acids. In particular, essential amino acids must be included in the culture media as cells cannot synthesize these by themselves. They are required for the proliferation of cells and their concentration determines the maximum achievable cell density. L-glutamine, an essential amino acid, is particularly important. L-glutamine provides nitrogen for NAD, NADPH and nucleotides and serves as a secondary energy source for metabolism. L-glutamine is an unstable amino acid, that, with time, converts to a form that cannot be used by cells, and can thus be added to media just before use. Caution should be used when adding more L-glutamine than is called for in the original medium formulation since its degradation results in the build-up of ammonia, and ammonia can have deleterious effect on some cell lines. L-glutamine concentrations for mammalian cell culture media can vary from 0.68 mM in Medium 199 to 4 mM in Dulbecco's Modified Eagles's Medium. Invertebrate cell culture media can contain as much as 12.3 mM L-glutamine. Supplements like glutamax are more stable and can replace glutamine for long term culturing of slow cells.

Nonessential amino acids may also be added to the medium to replace those that have been depleted during growth. Supplementation of media with non-essential amino acids stimulates growth and prolongs the viability of the cells.

Carbohydrates may also be added to cell culture media. Carbohydrates in the form of sugars are the major source of energy. Most of the media contain glucose and galactose, however, some contain maltose and fructose.

Cell culture media used herein may also include proteins and peptides. The most commonly used proteins and peptides are albumin, transferrin, and fibronectin. They are particularly important in serum-free media. Serum is a rich source of proteins and includes albumin, transferrin, aprotinin, fetuin, and fibronectin. Albumin is the main protein in blood acting to bind water, salts, free fatty acids, hormones, and vitamins, and transport them between tissues and cells. The binding capacity of albumin makes it a suitable remover of toxic substances from the cell culture media.

Cell culture media used herein may also include protective agents, such as aprotinin. Aprotinin is stable at neutral and acidic pH and resistant to high temperatures and degradation by proteolytic enzymes. It has the ability to inhibit several serine proteases such as trypsin. Fetuin is a glycoprotein found in fetal and newborn serum at larger concentrations than in adult serum. It is also an inhibitor of serine proteases. Fibronectin is a key player in cell attachment. Transferrin is an iron transport protein that acts to supply iron to the cell membrane.

The cell culture media used herein may also include vitamins and trace elements. Many vitamins are essential for growth and proliferation of cells. Vitamins cannot be synthesized in sufficient quantities by cells and are therefore important supplements required in tissue culture. Again serum is the major source of vitamins in cell culture, however, media are also enriched with different vitamins making them suitable for a particular cell line. The B group vitamins are most commonly added for growth stimulation. Trace elements are often supplemented to serum-free media to replace those normally found in serum. Trace elements like copper, zinc, selenium and tricarboxylic acid intermediates are chemical elements that are needed in minute amounts for proper cell growth. These micronutrients are essential for many biological processes, e.g. the maintenance of the functionality of enzymes.

The complete growth media recommended for certain cell lines also may require additional components which are not present in the basal media and serum. These components, supplements, help sustain proliferation and maintain normal cell metabolism, e.g., hormones, growth factors and signaling substances.

Growth media may also include antibiotics. Antibiotics are not required for cell growth but are often used to control the growth of bacterial and fungal contaminants. Routine use of antibiotics for cell culture is not recommended since antibiotics can mask contamination by mycoplasma and resistant bacteria. Moreover, antibiotics can also interfere with the metabolism of sensitive cells.

The selection of the media may depend on the type of cells to be cultured and also the purpose of the culture and resources available in the laboratory. Different cell types have highly specific growth requirements, therefore, the most suitable media for each cell type must be determined experimentally. In general, it is good to start with MEM for adherent cells and RPMI-1640 for suspension cells.

Examples of common cell culture media can be found commercially (SIGMA®, ATCC®, LIFE TECHNOLOGIES®) and are as follows:

Eagle's Minimum Essential Medium (EMEM): EMEM was among the first widely used media and was formulated by Harry Eagle from a simpler basal medium (BME). EMEM contains balanced salt solution, nonessential amino acids, and sodium pyruvate. It is formulated with a reduced sodium bicarbonate concentration (1500 mg/l) for use with 5% $CO_2$. Since EMEM is a non-complex medium, it is generally fortified with additional supplements or higher levels of serum making it suitable for a wide range of mammalian cells.

Dulbecco's Modified Eagle's Medium (DMEM). DMEM has almost twice the concentration of amino acids and four times the amount of vitamins as EMEM, as well as ferric nitrate, sodium pyruvate, and some supplementary amino acids. The original formulation contained 1,000 mg/L of glucose and was first reported for culturing embryonic mouse cells. A further variation with 4500 mg/L of glucose has been proved to be optimal for culture of various types of cells. DMEM is a basal medium and contains no proteins or growth promoting agents. Therefore, it requires supplementation to be a "complete" medium. It is most commonly supplemented with 5-10% Fetal Bovine Serum (FBS). DMEM utilizes a sodium bicarbonate buffer system (3.7 g/L) and therefore requires artificial levels of $CO_2$ to maintain the required pH. Powdered media is formulated without sodium bicarbonate because it tends to gas off in the powdered state. Powdered media requires the addition of 3.7 g/L of sodium bicarbonate upon dissolving it in water. DMEM was used initially for the culture of mouse embryonic stem cells. It has been found to be widely applicable in primary mouse and chicken cells, viral plaque formation and contact inhibition studies.

RPMI-1640. RPMI-1640 is a general purpose media with a broad range of applications for mammalian cells, especially hematopoietic cells. RPMI-1640 was developed at Roswell Park Memorial Institute (RPMI) in Buffalo, New York. RPMI-1640 is a modification of McCoy's 5A and was developed for the long-term culture of peripheral blood lymphocytes. RPMI-1640 uses a bicarbonate buffering system and differs from the most mammalian cell culture media in its typical pH 8 formulation. RPMI-1640 supports the growth of a wide variety of cells in suspension and grown as monolayers. If properly supplemented with serum or an adequate serum replacement, RPMI-1640 has a wide range of applications for mammalian cells, including the culture of fresh human lymphocytes, fusion protocols, and growth of hybrid cells.

The above-described cell culture and microbial growth media are not intended to be limiting on the scope and range of possible media that may be used with the instant invention. The skilled person will be able to consider appropriate media options based on the totality of circumstances and make an appropriate selection.

In addition, bioprocess systems may also include other components to facilitate a bioprocess, depending on the type. For example, various enzymes and surfactants can be added.

For example, enzymes, such as cellobiases and cellulases, are used in some bioprocesses. Cellobiases include a cellobiase from *Aspergillus niger* sold under the tradename NOVOZYME 188™. A cellulase may be of fungal or bacterial origin. Cellulases include those from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum*, and *Acremonium furatum*; preferably from the species *Humicola insolens* DSM 1800, *Fusarium oxysporum* DSM 2672, *Myceliophthora thermophila* CBS117.65, *Cephalosporium* sp. RYM-202, *Acremonium* sp. CBS 478.94, *Acremonium* sp. CBS 265.95, *Acremonium persicinum* CBS169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS157.70, *Acremonium roseogriseum* CBS134.56, *Acremonium incoloratum* CBS146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Enzyme complexes may be utilized, such as those available from Genencore under the tradename ACCELLERASE®, for example, Accellerase® 1500 enzyme complex. Accellerase 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of Accellerase® 1500 enzyme complex and NOVOZYME™ 188 cellobiase is used.

The addition of surfactants can enhance the rate of some bioprocesses. Examples of surfactants include non-ionic surfactants, such as a Tween® 20 or Tween® 80 polyethylene glycol surfactants, ionic surfactants, or amphoteric surfactants. Other suitable surfactants include octylphenol ethoxylates such as the TRITON™ X series nonionic surfactants commercially available from Dow Chemical. A surfactant can also be added to keep a product that is being produced in solution, particularly in high concentration solutions.

Bioreactor Products and Purification

The bioreactors described herein can by utilized to produce any type of biologic product, including vaccines, blood and blood components, allergenics, gene therapy components, tissues, and recombinant therapeutic proteins. Biologics can be composed of sugars, proteins, or nucleic acids or complex combinations of these substances, or may be living entities such as cells and tissues. Therapeutic proteins include, but are not limited to, monoclonal antibodies, bi-specific antibodies, enzymes, cytokines, hormones, and fusion proteins.

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

In various embodiments, the bioreactors described herein can be used to produce antibody therapeutics. Antibodies within the scope of the present invention include, but are not limited to: anti-HER2 antibodies including Trastuzumab (HERCEPTIN®) (Carter et al., Proc. Natl. Acad. Sci. USA, 89:4285-4289 (1992), U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108, B1, or Tositumomab (BEXXAR®)); anti-IL-8 (St John et al., Chest, 103:932 (1993), and International Publication No. WO 95/23865); anti-VEGF antibodies including humanized and/or affinity matured anti-VEGF antibodies such as the humanized anti-VEGF antibody huA4.6.1 AVASTIN® (Kim et al., Growth Factors, 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., Transplant Intl. 4:3-7 (1991), and Hourmant et al., Transplantation 58:377-380 (1994)); anti-IgE (Presta et al., J. Immunol. 151:2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. J. Immunol. 156(4):1646-1653 (1996), and Dhainaut et al. Crit. Care Med. 23(9):1461-1469 (1995)); anti-Tissue Factor (TF) (European Patent No. 0 420 937 B1 granted Nov. 9, 1994); anti-human α4β7 integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. Arthritis Rheum 39(1):52-56 (1996)); anti-CD52 antibodies such as CAMPATH-1H (Riechmann et al. Nature 332:323-337 (1988)); anti-Fc receptor antibodies such as the M22 antibody directed against FcγRI as in Graziano et al. J. Immunol. 155(10):4996-5002 (1995); anti-carcinoembryonic antigen (CEA) antibodies such as hMN-14 (Sharkey et al. Cancer Res. 55(23Suppl): 5935s-5945s (1995); antibodies directed against breast epithelial cells including huBrE-3, hu-Mc 3 and CHL6 (Ceriani et al. Cancer Res. 55(23): 5852s-5856s (1995); and Richman et al. Cancer Res. 55(23 Supp): 5916s-5920s (1995)); antibodies that bind to colon carcinoma cells such as C242 (Litton et al. Eur J. Immunol. 26(1):1-9 (1996)); anti-CD38 antibodies, e.g. AT 13/5 (Ellis et al. J. Immunol. 155(2):925-937 (1995)); anti-CD33 antibodies such as Hu M195 (Jurcic et al. Cancer Res 55(23 Suppl):5908s-5910s (1995) and CMA-676 or CDP771; anti-CD22 antibodies such as LL2 or LymphoCide (Juweid et al. Cancer Res 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PR0542; anti-hepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

Any suitable method for purification of bioreactor products is contemplated. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their antibody/antigen affinity, charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Affinity chromatography, which exploits a specific interaction between the protein to be purified and an immobilized capture agent, may also be an option for some proteins. Protein A is a useful adsorbent for affinity chromatography of proteins, such as antibodies, which contain an Fc region. Protein A is a 41 kD cell wall protein from *Staphylococcus aureas* which binds with a high affinity (about 10-8M to human IgG) to the Fc region of antibodies.

Proteins may be purified using controlled pore glass (Sulkowski, E. Protein Purification: Micro to Macro, pgs 177-195 (1987); Chadha et al. Preparative Biochemistry 11(4):467-482 (1981)) or underivatized silica (Reifsnyder et al. J. Chromatography 753:73-80 (1996)).

The protein to be purified using the method described herein is generally produced using recombinant techniques. Methods for producing recombinant proteins are described, e.g., in U.S. Pat. Nos. 5,534,615 and 4,816,567, specifically incorporated herein by reference. In preferred embodiments, the protein of interest is produced in a CHO cell (see, e.g. WO 94/11026). Examples of proteins which can be purified using the process described herein have been described above.

In certain embodiments (e.g., antibody production), purification can be achieved using Protein A-based means. Protein A immobilized on a solid phase is used to purify the CH2/CH3 region-containing protein. The solid phase is preferably a column comprising a glass, silica, agarose or polystyrene surface for immobilizing the Protein A. Preferably, the solid phase is a controlled pore glass column or a silicic acid column. Sometimes, the column has been coated with a reagent, such as glycerol, in an attempt to prevent nonspecific adherence to the column. The PROSEP A™ column, commercially available from Bioprocessing Limited, is an example of a Protein A controlled pore glass column which is coated with glycerol. Other examples of columns contemplated herein include the POROS 50 A™ (polystyrene) column or rProtein A SEPHAROSE FAST FLOW™ (agarose) column.

The solid phase for the Protein A chromatography is equilibrated with a suitable buffer. For example, the equilibration buffer may be 25 mM Tris, 25 mM NaCl, 5 mM EDTA, pH 7.1.

The contaminated preparation derived from the recombinant host cells is loaded on the equilibrated solid phase using a loading buffer which may be the same as the equilibration buffer. As the contaminated preparation flows through the solid phase, the protein is adsorbed to the immobilized Protein A and other contaminants (such as Chinese Hamster Ovary Proteins, CHOP, where the protein is produced in a CHO cell) may bind nonspecifically to the solid phase.

The next step performed sequentially may entail removing the contaminants bound to the solid phase, antibody and/or Protein A, by washing the solid phase in an intermediate wash step. After loading, the solid phase may be equilibrated with equilibration buffer before beginning the intermediate wash step. The intermediate wash buffer may comprise salt and a further compound, where the further compound is (a) detergent (preferably polysorbate, e.g. polysorbate 20 or polysorbate 80); (b) solvent (preferably hexylene glycol); and (c) polymer (preferably PEG). The salt employed may be selected based on the protein of interest, but preferably is acetate (e.g. sodium acetate), especially where the antibody is an anti-HER2 antibody such as Trastuzumab; or citrate (e.g., sodium citrate), especially where the antibody is an anti-IgE antibody such as E26. The amounts of the salt and further compound in the composition are such that the combined amount elutes the contaminant(s), without substantially removing the protein of interest. Preferred salt concentrations in such wash buffers are from about 0.1 to about 2M, and more preferably from about 0.2M to about 0.6M. Useful detergent concentrations are from about 0.01 to about 5%, more preferably from about 0.1 to 1%, and most preferably about 0.5%, e.g. where the detergent is polysorbate. Exemplary solvent concentrations are from about 1% to 40%, preferably from about 5 to about 25%. For instance, in the examples herein, the preferred concentration of the solvent (hexylene glycol) for E26 was about 20%, whereas for Trastuzumab the preferred concentration of the solvent (again hexylene glycol) was about 10%. Where the further compound is a polymer (e.g. PEG 400 or PEG 8000), the concentration thereof may, for example, be from about 1% to about 20%, preferably from about 5% to about 15%.

The eluted protein preparation may be subjected to additional purification steps either prior to, or after, the Protein A chromatography step. Exemplary further purification steps include hydroxylapatite chromatography; dialysis; affinity chromatography using an antibody to capture the protein; hydrophobic interaction chromatography (HIC); ammonium sulphate precipitation; anion or cation exchange chromatography; ethanol precipitation; reverse phase HPLC; chromatography on silica; chromatofocusing; and gel filtration. In the examples herein, the Protein A chromatography step is followed by downstream cation exchange (SP-Sepharose) and anion exchange (Q-Sepharose) purification steps.

The protein thus recovered may be formulated in a pharmaceutically acceptable carrier and is used for various diagnostic, therapeutic or other uses known for such molecules.

Pharmaceutical Compositions of Bioreactor Products

The products produced by the bioreactors of the invention can be mixed with a pharmaceutically acceptable carrier (excipient), including buffer, to form a pharmaceutical composition for use in alleviating a disease or disorder. "Acceptable" means that the carrier must be compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover. In one example, a pharmaceutical composition described herein contains more than one anti-HLA-DQ8 antibodies that recognize different epitopes/residues of the target antigen.

The pharmaceutical compositions can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing a bioreactor product, which can be prepared by any suitable method, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The bioreactor products may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing a bioreactor product (e.g., an antibody) with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

EXAMPLES

Example 1. Silicone-Based Membranes for Bubble-Free Gas Transfer in High Density Bioreactor Cultures Recent technology development has allowed cell culture to achieve very high cell density which results in high productivity of monoclonal antibodies. [1] However, control of dissolved oxygen (DO) in these bioprocesses remains challenging as high levels of oxygen and carbon dioxide transfer are required to support high density cultures. To achieve high transfer, methods such as microsparging, where micron-sized bubbles are released into the reactor, are employed. [2] However, the use of microsparging can increase bubble-burst associated cell death and the risk of bioreactor foam-out, which may lead to premature run termination and loss of product. [3, 4] Further, the addition of antifoams and shear protectants to prevent foam-out and bubble-burst cell death are in extreme cases required to be added at levels that may be toxic to cells. [5]

To eliminate challenges associated with bubble sparging, bubble-free aeration with porous and non-porous membranes has been investigated for cell culture applications. Polymeric membranes with micron-sized pores have been described in bubble-free aeration, where the balance of pressure between culture and gas allow bubble-free transfer at the gas-liquid interface through pores in the membrane. [6-8] Additionally, the use of hydrophobic membranes, which prevents pore-wetting, have demonstrated enhanced transfer compared to hydrophilic membranes as liquid entrapped within pores creates an additional barrier for gas transfer to the culture. [9] Non-porous silicone polymer-based membranes (e.g., polydimethylsiloxane, PDMS) have also been used for bubble-free gas transfer, where gas molecules diffuse through the dense polymer and transfer to the culture at the membrane-culture contact surface. [10-12] While porous and non-porous membranes have been applied in cell culture, only low densities have been achieved (<20e6 cells/mL) due to limitations in membrane design and challenges associated with membrane operation. [13] Specifically, if the gas and culture pressures are improperly balanced in porous membranes, micron-sized bubbles can form and risk bubble-burst cell death and bioreactor foam-out. In non-porous membranes, the silicone-based tubing used is thick, thus transfer of gas molecules through the polymer is slow, preventing sufficient gas exchange to support high density cultures. To overcome challenges associated with bubble sparging and support high density cultures, alternate methods and materials for bubble-free gas exchange are needed.

A new type membrane has been developed with properties that may permit enhanced gas transfer to support high density cultures. [14] These membranes contain small (ID 190 um, OD 300 um), thin-walled (55 um) PDMS hollow fibers packed in bundles and potted inside a unit that may be attached to bioreactors via an external recirculation loop for gas transfer. Gas is sent through the hollow fiber lumen, culture liquid is passed through the shell-side of the membrane unit, and gas transfer occurs at the PDMS-liquid contact surface. Here, the use of these membranes for gas transfer in high density perfusion cultures (>20e6 cells/mL) is described.

Studies to determine kLa (mass transfer coefficient) demonstrated comparable oxygen ($O_2$) mass transfer efficiency between membranes with 2500 cm$^2$ surface area and microspargers in 2 liter (L) bioreactors. Enhanced mass transfer was achieved by increasing the recirculation flow rate, suggesting optimization work can be done to further elucidate the potential of this membrane. In addition to $O_2$ transfer, air passed through the lumen of the membranes removes carbon dioxide ($CO_2$) at rates comparable to drilled hole sparging, indicating potential use of the membrane to eliminate all sparging in bioreactors. To determine whether these membranes provide sufficient DO to sustain high density CHO cell cultures, several cell culture experiments were conducted. In the first experiment, a single membrane was attached to the bioreactor to replace microsparging for $O_2$ addition (drilled hole sparging was used to strip $CO_2$). DO was maintained at 60% over the course of several weeks and supported culture densities of 40e6-120e6 cells/mL. In a subsequent experiment, a bubble-free bioreactor setup was tested, where two membranes were placed in series, one for $CO_2$ stripping and the other for oxygenation. Cell densities of 20-30e6 cells/mL were maintained during the course of weeks in culture with sufficient oxygen delivery and p$CO_2$ below 120 mmHg. Using this technology, high cell density bioreactor cultures may be improved by removing the need for added shear protectants and anti-foam agents, which may have detrimental impact on cultures. Further, if deemed successful to replace sparging, these membranes would be a revolutionary way to enable high cell density culture in both perfusion and fed-batch systems.

Methods/Experiments

An initial test for gas exchange with silicone membranes was conducted on a 100 L SUB use bioreactor bag (SUB), filled with 65 L of water. A 2.1 m$^2$ PDMS membrane (PermSelect® silicone hollow fiber modules) was attached to the recirculation loop of the SUB. 5 LPM of water was recirculated through the membrane shell side. A DO probe was inserted into the SUB to monitor oxygen transfer. Prior to measurements for $O_2$ addition, N2 was flowed through the membrane lumen to remove $O_2$ from the reactor (% DO<20%). Then, $O_2$ was flowed through the membrane at different rates (0.1 LPM, 1 LPM). To compare, 0.1 and 1 LPM of $O_2$ was also flowed through the porous sparger (15 μm) in the SUB.

For kLa studies, a 2500 cm$^2$ PDMS membrane (PermSelect® silicone hollow fiber modules) was attached to the recirculation loop of a 2 L glass bioreactor. 2 L of phosphate buffered saline (PBS) with 1 g/L poloxamer 188 (pluronic) was heated to 37 and recirculated through the shell-side of the membrane with a centrifugal pump (Levitronix) at different flow rates (Table 1). A DO probe (Hamilton Visi-ferm) and a $CO_2$ probe (Mettler Toledo) were attached to the bioreactor to monitor gas transfer. Prior to measurements for $O_2$ addition, N2 was flowed through the membrane to remove $O_2$ from the reactor (% DO<10%). For $O_2$ addition, air was flowed through the membrane at different rates until saturation (% DO levels off, ~100%). To compare membrane gas exchange to traditional sparging, air was also flowed through a drilled hole sparger and microporous sparger (15 um pores) at different flow rates. Prior to $CO_2$ removal, 10% $CO_2$ mixed with air was flowed through the membrane (p$CO_2$>55 mmHg). For $CO_2$ stripping, air was flowed through the membrane at different rates until stabilization of $CO_2$ reached (p$CO_2$ Levels off, ~1-2 mmHg). To compare with traditional $CO_2$ stripping methods, air was flowed through a drilled hole sparger at different rates to determine kLa. kLa was determined for the different conditions tested as follows:

In the absence of cells, $$\frac{dC}{dt} = k_L a(C^* - C)$$

$$\text{Then, } \ln\left(\frac{C^* - C_s}{C^* - C_t}\right) = k_2 at$$

Thus, the slope of $$\ln\left(\frac{C^* - C_a}{C^* - C_t}\right) vst = k_L a$$

Where C* is the gas concentration (% DO or mmHg) at saturation (average of last 10 points of measurement at saturation), $C_0$ is the initial gas concentration, and $C_t$ is the gas concentration at time t.

Steady-State to Unsteady-State Operation.

To determine if silicone-based membranes can be used as a replacement for microsparging, a 2500 cm2 membrane (PermSelect® silicone hollow fiber modules) was attached to the recirculation loop of a perfusion culture bioreactor, after the hollow fiber (FIG. 1C). A proprietary CHO cell line (CHO1), seeded at 10e6 cells/mL was grown to 40e6 cells/mL (3 days) and a cell bleed started to maintain density at 40e6 cells/mL. The y-off to the membrane remained closed during ramp up to density and during the first 4 days of steady-state operation, and % DO was maintained at 60% with microsparging and drilled hole sparging. After 4 days of steady-state operation, 50% of the recirculation (0.8 LPM total, 0.4 LPM=50%) was sent through the membrane. Additionally, the microsparger was turned off and the $O_2$ gas line was switched to the membrane to provide 0-0.1 LPM oxygen to maintain % DO at 60%. Finally, the drilled hole sparger (for $CO_2$ stripping) remained on, but the gas mixture was switched from 0.5 LPM $O_2$ to 0.25 LPM $O_2$+0.25 LPM air. Cells were cultured for 3 days with this setup at $40\times10^6$ cells/mL with the membrane to determine if possible to maintain DO during culture and have minimal impact to cells. After 3 days of steady state operation, the cell bleed was lowered and cell density increased to $120\times10^6$ cells/mL to determine if the membrane could support higher density cultures. Viability and LDH were monitored to determine culture health during operation. % DO (dissolved oxygen) was monitored to determine if sufficient $O_2$ was supplied to cells via membrane gas exchange.

Ramp-Up and Operation at High Cell Densities.

As a second test to determine the effects of the membrane on culture during ramp up to high cell densities, a 2500 cm² membrane (PermSelect® silicone hollow fiber modules) was attached to the recirculation loop of a perfusion culture bioreactor, after the hollow fiber. Half of the total recirculation (0.8 LPM total, 0.4 LPM=50%) was directed through the membrane from day 0 of culture. CHO1 was seeded at 10e6 was grown in non-steady-state operation to determine effects of the membrane during ramp-up to density and maximum density supported by the membranes. A mixture of 0.25 LPM air+0.25 LPM $O_2$ was sent through the drilled hole sparger (for $CO_2$ stripping). 0-0.1 LPM $O_2$ was sent through the membrane to supply $O_2$ to maintain % DO at 60% during culture. Viability and LDH were monitored to determine culture health during operation. % DO was monitored to determine if sufficient $O_2$ was supplied to cells via membrane gas exchange.

Bubble-Free Aeration in High Density Perfusion Culture

Based on kLa experiments for $O_2$ addition and $CO_2$ stripping and replacing the microsparger in high density cultures, a bubble-free setup (FIG. 1D) was tested to determine if possible to operate without sparging. Two 2500 cm2 membranes (PermSelect® silicone hollow fiber modules) were attached to the recirculation loop of a perfusion culture reactor, after the hollow fiber. The first membrane was used for $CO_2$ stripping and pH control, with a mixture of air, $O_2$, and $CO_2$ flowed through to control pH during low density culture and later switched to a mixture of air and $O_2$ to strip $CO_2$ during high density culture. The second membrane was used for supplemental $O_2$ addition to support DO at 60% during culture. 0.1 LPM air was flowed to the headspace of the reactor to provide positive pressure to the bioreactor. Table 4 contains a list of gas flows used each day during culture in each membrane. A proprietary CHO cell line (CHO2), seeded at 1e6 cells/mL in a 2 L bioreactor was grown to 30e6 cells/mL and maintained at 25e6-30e6 cells/mL with a cell bleed. During ramp-up to density, for the first 6 days, half of the recirculation flow (0.8 LPM total, 0.4 LPM=50%) was directed through the membranes. On day 7, DO was not sustained by 0.4 LPM recirculation flow, so 100% of the recirculation (0.8 LPM) was sent through the membranes to strip $CO_2$ and add $O_2$. Viability and LDH were monitored to determine culture health during operation. % DO was monitored to determine if sufficient $O_2$ was supplied to cells via membrane gas exchange.

Results and Discussion

Determination of $O_2$ Addition with Membrane Gas Exchange

To initially test gas transfer using nonporous PDMS membranes, a membrane with 2.1 m² transfer surface area was attached to the recirculation loop of a 100 L SUB. The SUB was filled with 65 L of water which was recirculated through the membrane at 5 LPM. More rapid gas transfer was observed with the membrane (FIG. 10) compared to the built in sparger and may be attributed to the large surface area (2.1 m2) of fibers within the membrane unit. These results encouraged further investigation of $O_2$ addition with membranes and determination of gas transfer coefficients (kLa) compared to traditional sparging methods.

Drilled hole and microporous sparging are commonly employed in high density cultures to provide sufficient DO, however bubble-burst associated cell death and reactor foam outs can cause premature run termination and product loss. To determine if bubble-free membrane gas exchange compares to these sparging methods, a small-scale, 2 L bioreactor was set up with model fluid (PBS+1 g/L Pluronic) and oxygen addition monitored for different air flow rates and constant recirculation flow rate (0.8 LPM) through flow path "B" (FIG. 3). kLa was highest with microsparging, however membrane gas transfer achieved transfer coefficients on the same order of magnitude of microsparging. Drilled hole sparging was associated with the slowest $O_2$ addition and lowest kLa. However, it is important to note that while drilled hole sparging may be used for oxygen addition, its function is primarily for $CO_2$ stripping as discussed in the next section.

TABLE 1 kLa for drilled hole sparging, microsparging, and membrane gas exchange for different air flow rates.

| Test | Sparge Type | Air Flow (LPM) | kLa (hr$^{-1}$) |
|---|---|---|---|
| 1 | Drilled Hole | 0.1 | 1.9 |
| 2 | Drilled Hole | 0.25 | 2.8 |
| 3 | Microsparger | 0.1 | 30.0 |
| 4 | Microsparger | 0.25 | 35.3 |
| 5 | Membrane | 0.1 | 11.6 |
| 6 | Membrane | 0.25 | 19.3 |

Initial comparison of membrane gas transfer to sparging was performed using a single recirculation flow rate (0.8 LPM) and flow path. Additional studies were conducted to determine if different flow paths (FIG. 3) and recirculation rates could enhance membrane gas transfer to be comparable to microsparging in the 2 L model bioreactor setup described previously (2500 cm² membrane). For flow path "A", no differences were observed in kLa with change in recirculation rate. This may result from liquid unable to flow into the densely packed bundle of PDMS membrane fibers at the center of the unit so less transfer occurs (Table 2). In flow path "B", kLa increased with increasing flow rate, indicating that faster flows permit more rapid gas exchange. Additionally, at high flow rates, kLa comparable to microsparging was observed. Last, higher kLa was achieved for lower flows in flow path "C" compared to flow path "B". These results indicate that much of the shell side flow in "B" may leave the first outlet port, reducing the time for liquid contacting the fibers and lowering gas transfer.

While flow path "C" appears optimal for gas exchange in the membranes, recirculation flow was restricted in both paths "A" and "C". Membrane damage and rupture due to increased pump speed and pressure drop (FIG. 11) was observed for recirculation flows greater than 0.5 LPM. If transfer is to be improved with membranes, alternate membrane designs and flow paths should be investigated that minimize pressure drop and chance for membrane rupture. Further, high flow rates may cause shear to cells in culture, thus additional designs that reduce shear while providing high kLa need to be determined.

TABLE 2

Conditions and kLa tested for 2L offline models of $O_2$ addition.
Air flow was 0.25 LPM for all tests (also see FIG. 3D)

| Test Number | Recirculation (LPM) | Flow Path | kLa (hr$^{-1}$) |
| --- | --- | --- | --- |
| 1 | 0.2 | A | 5.02 |
| 2 | 0.4 | A | 4.66 |
| 3 | 0.5 | A | 5.06 |
| 4 | 0.2 | B | 7.52 |
| 5 | 0.4 | B | 13.16 |
| 6 | 0.5 | B | 15.9 |
| 7 | 0.8 | B | 18.72 |
| 8 | 1 | B | 20.37 |
| 9 | 1.2 | B | 24.19 |
| 10 | 1.4 | B | 25.73 |
| 11 | 1.6 | B | 27.31 |
| 12 | 1.8 | B | 28.6 |
| 13 | 0.2 | C | 12.69 |
| 14 | 0.4 | C | 18.67 |
| 15 | 0.5 | C | 19.53 |

Determination of $CO_2$ Stripping with Membrane Gas Exchange

In order to operate a bioreactor with bubble-free gas exchange at high cell densities, $CO_2$ removal through membranes is required. Here, $CO_2$ stripping with air at different flow rates through membranes was compared to stripping with drilled hole sparging (Table 3). In the 2 L model bioreactor system, 10% $CO_2$ mixed with air was added to the bioreactor prior to stripping. Subsequently, the $CO_2$ was removed by sparging 100% air through the membrane or drilled hole sparger at different flow rates while keeping recirculation rate constant (0.4 LPM). Faster $CO_2$ stripping was observed in membranes compared to drilled hole sparging. This may be attributed to the membrane's enhanced N2 transfer (~78% N2 in air) and large surface area for transfer. These results are promising for future application in bubble-free bioreactor operation. As with $O_2$ transfer, optimal membrane design needs to be determined to allow increased recirculation flow rates to improve gas transfer while having low shear.

TABLE 3

Conditions and kLa tested for 2L offline models of $CO_2$ stripping. Note that flow path "B" (FIG. 3) was used for $CO_2$ stripping tests.

| Test | Sparge Type | Air Flow (L/min) | kLa (h−1) |
| --- | --- | --- | --- |
| 1 | Membrane | 0.25 | 1.89 |
| 2 | Membrane | 0.4 | 2.19 |
| 3 | Drilled Hole Sparger | 0.25 | 1.35 |
| 4 | Drilled Hole Sparger | 0.4 | 1.77 |

Replacing the Microsparger with Membrane Gas Exchange

Bubble sparging can negatively impact culture health while also increasing risk for foam-out and bioreactor loss. In particular, micron-sized bubbles formed by microporous spargers are considered a major contributor to cell death, where energy released during bubble burst lyses surrounding cells. Further, the foam generated by these bubbles is difficult to remove, and often requires large amounts of antifoaming agents to be added to bioreactors during culture. Additionally, at high densities, more microsparging is required, leading to more lysis and foam. Removal of microsparging from culture may help improve culture and lengthen bioreactor operation. Here, the investigation of using silicone-based membranes in place of microsparging during steady-state bioreactor operation and during ramp-up to high cell densities is described.

Steady-State to Unsteady-State Operation.

Figure 4A:
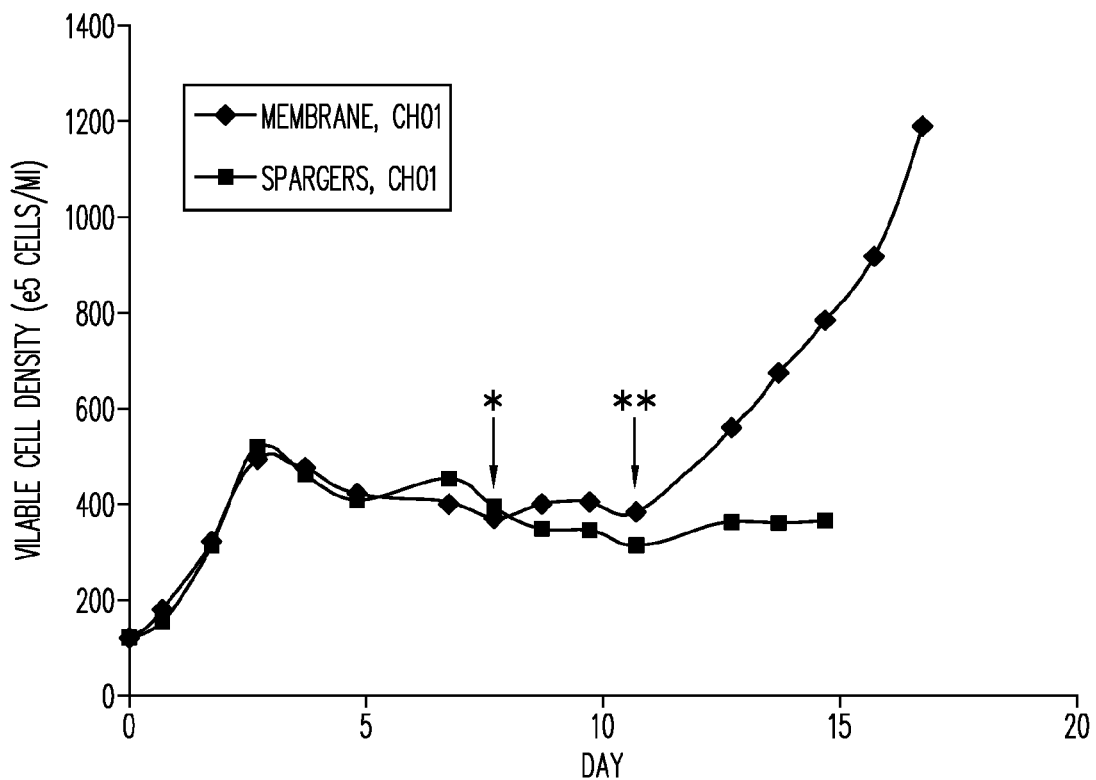
FIGS. 4A-4C show viable cell density (VCD), viability, and LDH of a proprietary CHO cell line (CHO1) cultured at steady to unsteady-state operation with membrane gas exchange replacing the microsparger, e.g., using the bioreactor system of FIG. 1B, FIG. 1C, or FIG. 1D.
Figure 4B:
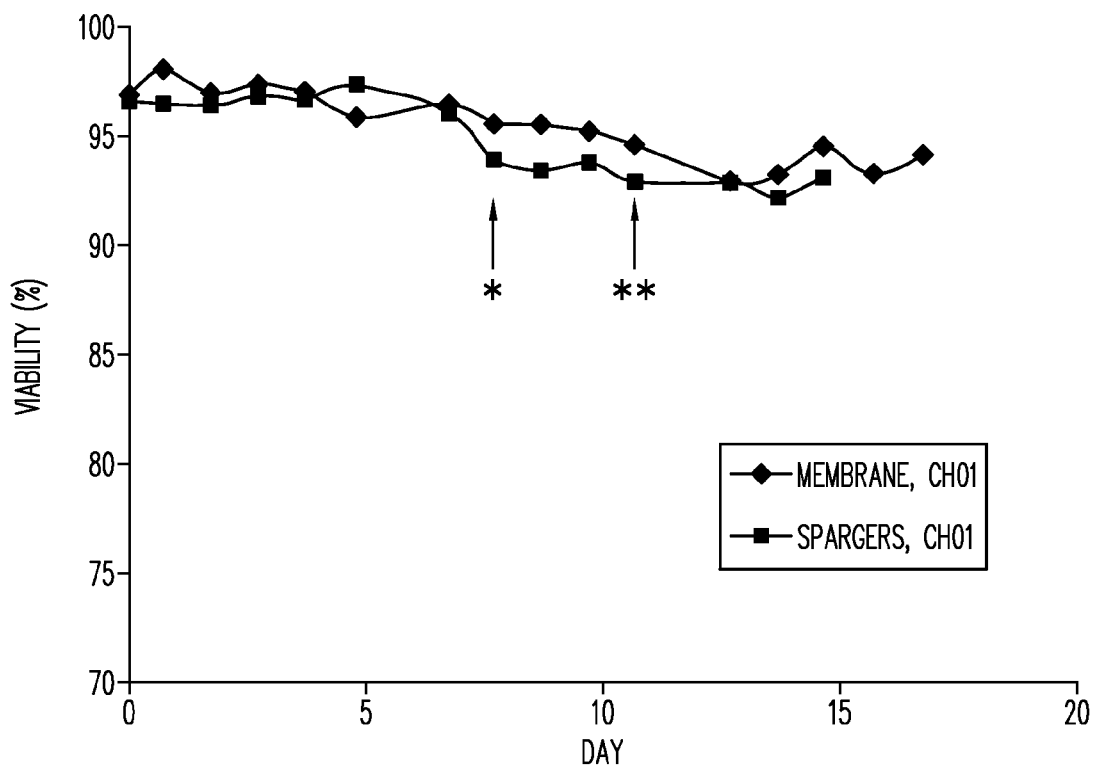
Figure 4C:
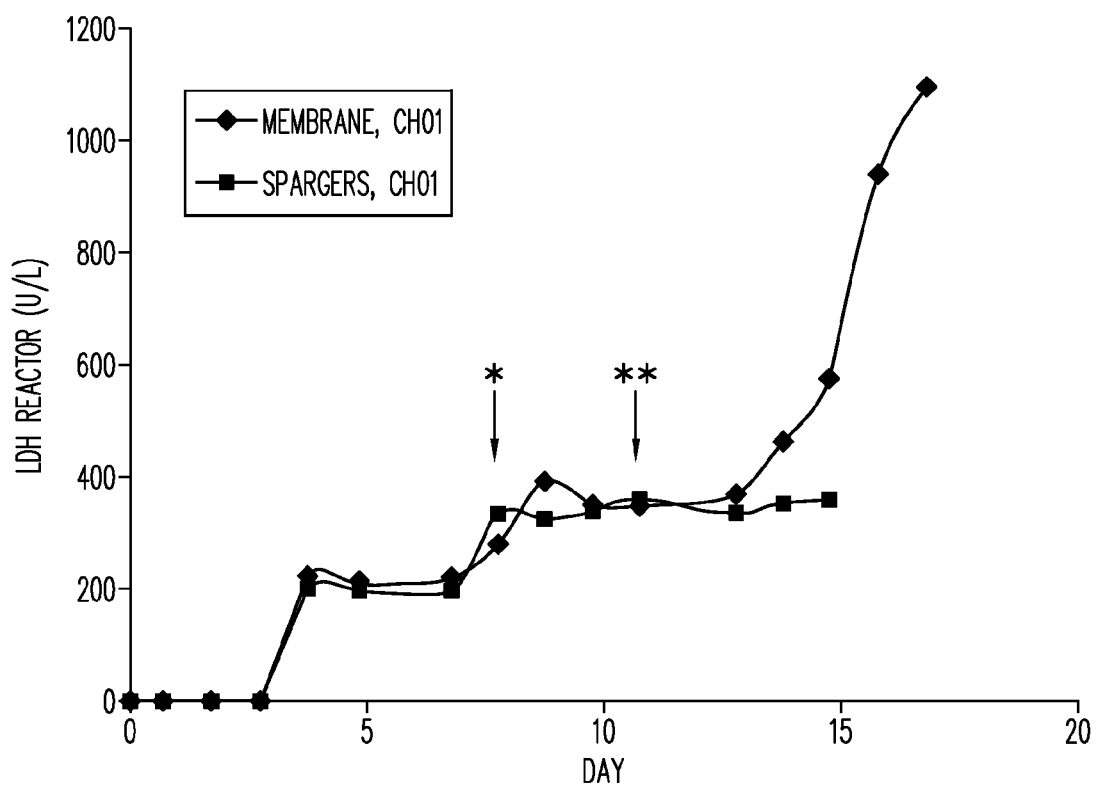
Figure 5A:
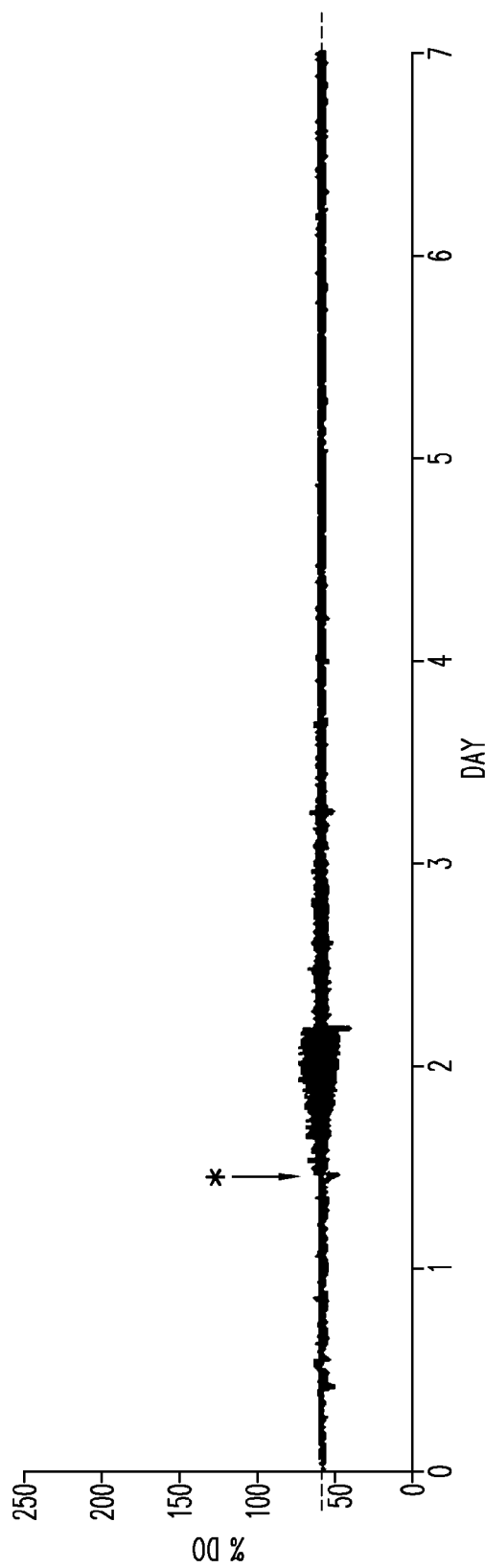
Figure 5C:
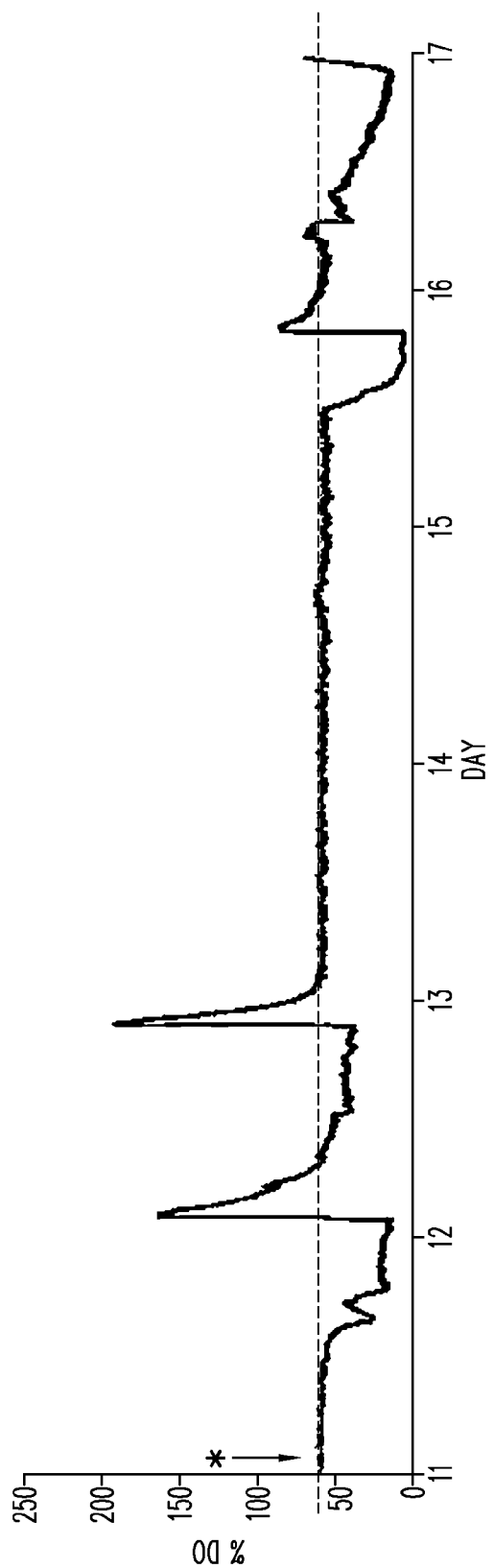

Initial tests to determine feasibility of replacing the microsparger with silicone membranes for gas exchange were conducted on steady-state cultures at high cell densities. A proprietary CHO cell line (CHO1) was cultured to densities of 40e6 cells/mL in a perfusion bioreactor with drilled hole sparging ($CO_2$ stripping+$O_2$ addition) and microsparging (supplemental $O_2$ addition) to sustain % DO at 60% (FIGS. 4A and 5A-5C). Once densities reached 40e6, the culture was maintained at 60% DO with standard sparging for four days to establish a baseline % DO profile (FIG. 5A). After 4 days, half of the 0.8 LPM culture recirculation flow (0.4 LPM) was redirected through the membrane, the $O_2$ from the microsparger was attached to the membrane gas exchanger, and a 0.25 LPM air with 0.25 LPM $O_2$ mixture was sent through the drilled hole sparger (FIG. 5B). DO was controlled by increasing or decreasing $O_2$ flow through the membrane (0-0.1 LPM) to sustain 60% DO. During startup of the membrane, DO fluctuated due to changes in response time using membranes as opposed to micro-bubbles, so the gain was decreased and integral increased to improve control over fluctuations (FIG. 5B). After steady-state operation with the membrane for 3 days, the cell bleed was reduced to increase density and determine if the membrane could sustain DO at higher densities. A density of 120e6 was achieved, however there were fluctuations in DO during ramp-up to higher densities (FIGS. 4A and 4C). It is hypothesized that water, which is also able to pass through these membranes, could block fibers and the filter at the gas outlet during operation and reduce gas transfer until higher gas flows push the water out of the fibers. Additional studies are required to determine if water blockage of the gas flow path causes these periods of reduced transfer during operation, or if the membrane is unable to control during unsteady-state operation. In addition to sustaining % DO during operation, there were no apparent effects of the membranes on culture health, with percent viability and lactate dehydrogenase (LDH) comparable to control (FIGS. 4B, 4C). Note that LDH increased when cell density was increased, which is believed to be primarily due to the presence of higher cell densities and not effects of the membrane on the culture. These results are promising for the application of membranes to replace microsparging in high density cultures. Moving forward, additional studies to understand the effects of membranes during ramp-up to high density were performed to better understand the effects of membranes on culture.

Ramp-Up and Operation at High Cell Densities.

Figure 6A:
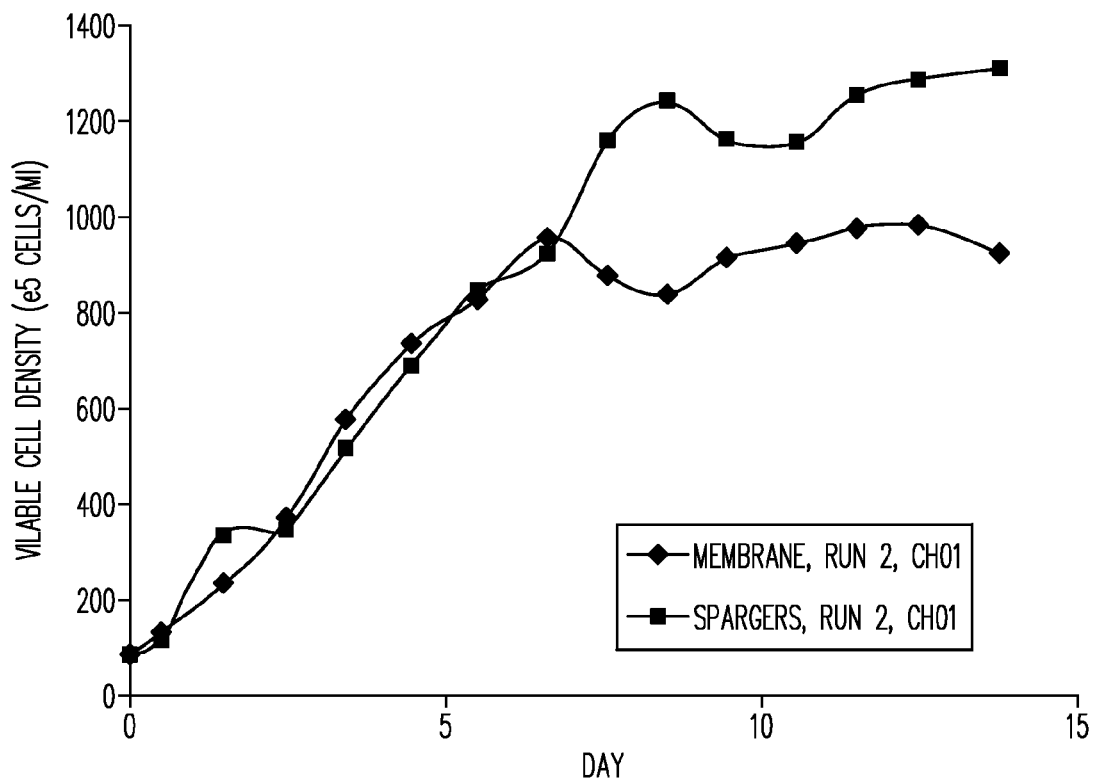
FIGS. 6A-6C show VCD (viable cell density), percent viability, and LDH (lactate dehydrogenase activity assay) of CHO1 cells cultured during ramp-up to high cell densities, e.g., using the bioreactor system of FIG. 1B, FIG. 1C, or FIG. 1D.
Figure 6B:
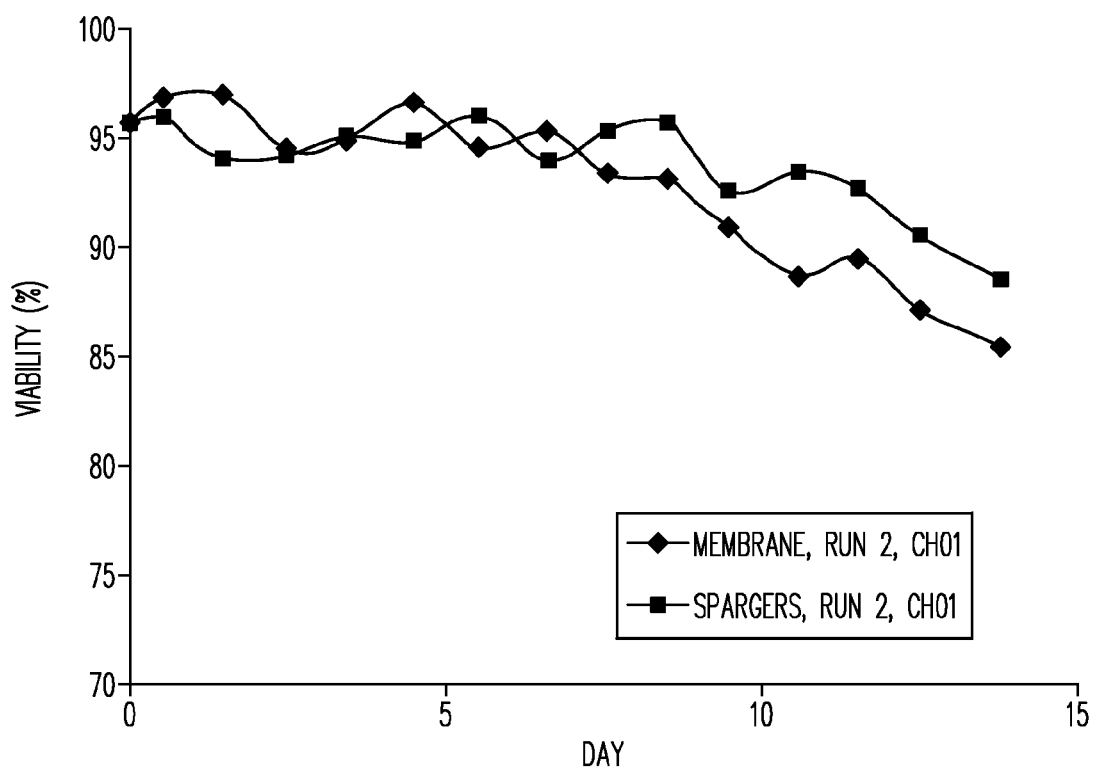
Figure 6C:
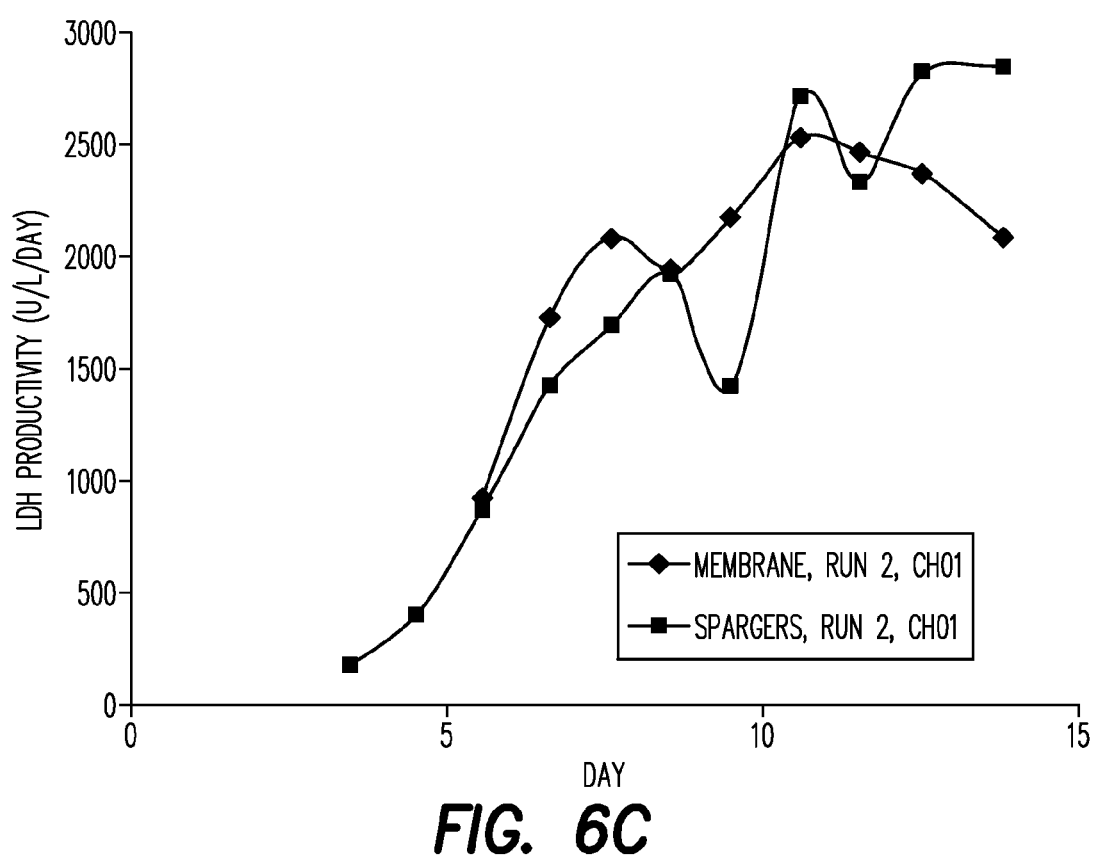

To determine if membranes could be used to control DO during ramp-up to high cell density, a membrane was placed downstream of the hollow fiber in the culture recirculation loop. Additionally, to prevent blockage of the fibers and gas outlet filter with water during operation, a sterile vent bottle was attached to the gas outlet of the membrane unit. Prior to inoculation with cells, half of the 0.8 LPM recirculation flow (0.4 LPM) was directed through the membrane. Cells were inoculated at 10e6 cells/mL and cultured to high densities without a cell bleed. Viability using the membrane was comparable to a control reactor with traditional sparging (FIG. 6B). However, densities only reached ~100e6 cells/mL compared to ~130 e6 cells/mL with traditional sparging, indicating that the membrane may have some effect on cells during ramp-up to density (FIG. 6A). While higher cell densities are associated with higher LDH the LDH of the bioreactors was comparable, which may indicate some negative effects of the membrane on culture health during operation (FIG. 6C). It is hypothesized that the current membrane design, which contains densely-packed fibers may cause shear or damage to cell membranes which may slow their growth. If alternate membrane designs with improved flow path and more spacing between fibers are implemented, it may be possible to reduce shear and cell damage during membrane operation and achieve higher densities.

During culture, DO was controlled at 60% with drilled hole sparging and membrane gas exchange. Initially, 0.25 LPM air through the drilled hole sparger was replaced with $O_2$ to 0.5 LPM. Once $O_2$ through the drilled hole sparger was maxed out (0.5 LPM), additional $O_2$ was supplied through the membrane from 0 to 0.1 LPM $O_2$ on demand. After DO control called for additional $O_2$ to be added through membrane exchanged, DO fluctuated around the 60% setpoint (FIG. 7). Changes to the PID control loop gain and integral did not reduce these fluctuations, indicating that the membrane is initially oversized for lower densities. As density increased, $O_2$ demand increased and fluctuations stabilized on day 5 FIG. 7A). Alternate control parameters may be implemented to reduce these fluctuations at low density. It is important to note that during the run, mass flow controller (MFC) failure occurred, affecting the DO profile and control. Specifically, from day 2-4, the oxygen through the drilled hole sparger periodically turned off, causing the membrane to be the only source of $O_2$. On day 3, the $O_2$ supply through the drilled hole sparger turned off and DO dropped to 0%, so gassing was temporarily switched to another MFC (manual DO control) to fix the original MFC (FIG. 7A, red). Control was returned to the original MFC on day 4-5; however, several additional fluctuations occurred mid-run as the MFC turned off briefly during operation (FIG. 7B, red). Further studies are needed to evaluate if the shear from the membrane as previously discussed or the loss in DO control with the malfunctioning MFC may have negatively impacted culture health and resulted in lower densities compared to the control. Additional tests are also required to determine if the vent bottle at the membrane gas outlet helps prevent DO fluctuations by allowing water to flow out of the fibers while preventing filter wetting. Despite challenges with MFC failure, the $O_2$ flow through the membrane never reached maximum flow (0.1 LPM) and was sufficient to sustain very high cell densities (~100e6 cells/mL at peak), which is promising for application of the membranes to replace microsparging in high density cultures.

Bubble-Free Bioreactor Operation

Removal of sparging from bioreactors may improve high density cultures, where removal of bubbles reduces bubble-burst-associated cell death and removes the need for antifoam addition. Here, two membranes were placed downstream of the hollow fiber (e.g., the "TFF (tangential flow filtration) Module" in FIG. 1D in a recirculation loop of a perfusion bioreactor (e.g., as depicted in FIG. 1D). The first membrane was used to replace the drilled hole sparger for $CO_2$ stripping and some oxygen addition, where a mixture of oxygen and air was sent through the lumen of the membrane unit. Additionally, the first membrane would supply $CO_2$ during low density operation at the beginning of culture to control pH. The second membrane was used only for oxygen addition to replace the microsparger as previously demonstrated. To challenge the membranes for bubble-free bioreactor operation, a second proprietary CHO cell line ($CHO_2$) with higher shear sensitivity and higher oxygen demand was used. Cells were inoculated at 1e6 cells/mL and cultured to a density of 30e6 cells/mL, when a cell bleed was applied to maintain steady-state operation of 25e6-30e6 cells/mL. The reactor was operated bubble-free for 17 days, with no addition of antifoam agents during operation. Additionally, DO was kept close to 60% during the entire operation period and never reached 0%, indicating that the membranes provided sufficient $O_2$ to sustain cultures.

Ramp-up to density in the bubble-free reactor was 1 day slower than the control reactor (ATF with drilled hole sparging+microsparging) and LDH was higher, indicating shear from the membrane may affect culture health (FIG. 8). While DO was largely maintained at 60%, control was not optimal and fluctuations occurred at different stages during culture (FIG. 9). $O_2$ demand of the CHO2 cell line is substantially higher than that of CHO1, and large flows of $O_2$ were required to be added during operation to sustain DO (Table 4). Specifically, $O_2$ demand continued to increase despite steady-state operation, and higher flows of $O_2$ had to be applied throughout the course of operation. Thus fluctuations in DO were caused during adjustments of the MFCs and oxygen flows. Additionally, at startup, half of the recirculation flow (0.4 LPM) was directed through the membrane. However, on day 7, all of the recirculation flow (0.8 LPM) was directed through the membrane to support the high oxygen demand. Finally, it is important to note that air is required to strip $CO_2$. Air was turned off between days 5 and 6 to supply enough $O_2$ one time during culture, however, $CO_2$ increased in response. It is hypothesized that the presence of N2 in air makes it more efficient at stripping, thus air or N2 will be required for $CO_2$ removal during bubble-free operation. In future bubble-free runs, MFCs that permit higher flows of oxygen will be investigated to optimize operation of the membrane unit.

TABLE 4

Recirculation flow rate and gas flow rates through membranes during bubble-free bioreactor operation. 0.1 LPM air was supplied to the headspace to provide positive pressure during operation.

| Day | Recirculation Rate (LPM) | Air Flow Rate, Membrane 1 (LPM) | O2 Flow Rate, Membrane 1 (LPM) | O2 Flow Rate, Membrane 2 (LPM) |
|---|---|---|---|---|
| 0 | 0.4 | 0.05 → 0.25 | 0 | 0 |
| 1-4 | 0.4 | 0.25 | 0 | 0 → 0.1 |
| 5 | 0.4 | 0.25 → 0 | 0 → 0.25 | 0 → 0.1 |
| 6 | 0.4 | 0.25 | 0 → 0.5 | 0 → 0.25 |
| 7 | 0.8 | 0.25 | 0.5 | 0 → 0.25 |
| 8 | 0.8 | 0.25 | 0.5 | 0.5 → 0.75 |
| 9-10 | 0.8 | 0.1 → 0.07 | 0.5 | 0.5 → 0.75 |
| 11-12 | 0.8 | 0.1 | 0.5 | 1 |
| 13 | 0.8 | 0.04 | 0.5 | 1 |
| 14 | 0.8 | 0.03 | 0.5 | 1 |
| 15-17 | 0.8 | 0.05 | 0.5 | 1.45 |

"→" signifies increasing or decreasing flow rate, controlling around the 60% DO set point. From day 6 to 7, all the MFCs maxed out gas flow rates (0.25 LPM Air + 0.5 LPM $O_2$; Membrane 2 = 0.25 LPM $O_2$), so recirculation flow was increased to 0.8 LPM. On day 9, due to issues establishing control over DO and the need to add additional $O_2$ from other MFCs, control was switched to manual.

CONCLUSIONS

A method for bubble-free gas transfer was described using silicone-based membrane units containing packed bundles of thin-walled hollow fibers. Transfer of $O_2$ through these membranes was sufficient to sustain 60% DO at high cell densities (100-120e6 cells/mL) without severe effects on culture health during operation. Bubble-free gas transfer was achieved with two membrane units, the first unit for stripping $CO_2$ and the second unit for $O_2$ addition. Cells remained viable for weeks in culture at high cell density (25-30e6 cells/mL) and DO was maintained close to 60% for the duration of bubble-free culture. Additionally, no antifoam was required in bubble-free cultures, which often sticks and forms a layer on vessel walls and hollow fibers during culture. In future studies, DO control will be optimized to reduce and prevent fluctuations during operation. Additionally, further investigation into the shear effects of these membranes is needed and additional designs to reduce shear will be identified. These studies are a primary investigation into the use of silicone-based membranes for gas transfer in high cell density cultures (>20e6 cells/mL) and have potential for application in both fed-batch and perfusion processes. Implementation of these membranes will mitigate many issues associated with traditional sparging, reducing the potential for premature run termination while operating at high density.

REFERENCES

The following references are cited within the present Application. Each is incorporate herein by reference in their entireties.
1. Kunert, R. and D. Reinhart, *Advances in recombinant antibody manufacturing*. Appl Microbiol Biotechnol, 2016. 100(8): p. 3451-61.
2. Qi, H., et al., The art & science of micro-sparging in high-density perfusion cultures of animal cells, in Animal Cell Technology: From Target to Market. 2001, Springer. p. 412-415.
3. Liu, Y., et al., Effects of bubble-liquid two-phase turbulent hydrodynamics on cell damage in sparged bioreactor. Biotechnol Prog, 2014. 30(1): p. 48-58.
4. Godoy-Silva, R., C. Berdugo, and J. J. Chalmers, Aeration, Mixing, and Hydrodynamics, Animal Cell Biroeactors, in Encyclopedia of Industrial Biotechnology: Bioprocess, Bioseparation, and Cell Technology, M. C. Flickinger, Editor. 2010, John Wiley & Sons, Inc.
5. Velugula-Yellela, S. R., et al., Impact of media and antifoam selection on monoclonal antibody production and quality using a high throughput micro-bioreactor system. Biotechnol Prog, 2018. 34(1): p. 262-270.
6. Wagner, R. and J. Lehmann, The growth and productivity of recombinant animal cells in a bubble-free aeration system. Tibtech, 1988. 6.
7. Buntemeyer, H., B. G. D. Bodeker, and J. Lehmann, *Membrane-stirrer-reactor for bubble free aeration and perfusion*. 1987: p. 411-419.
8. Lehmann, J., J. Vorlop, and H. Buntemeyer, *Bubble-free Reactors and Their Development for Continuous Culture with Cell Recycle*. Animal Cell Biotechnology, 1988. 3: p. 221-237.
9. Balgobin, R. and D. Karamanev, Bubble-free oxygen and carbon dioxide mass transfer in bioreactors using microporous membranes. 2012.
10. Velez-Suberbie, M. L., et al., Impact of aeration strategy on CHO cell performance during antibody production. Biotechnol Prog, 2013. 29(1): p. 116-26.
11. Emery, A. N., D. C. H. Jan, and M. Al-Rubeai, *Oxygenation of intensive cell-culture system*. Appl Microbiol Biotechnol, 1995. 43: p. 1028-1033.
12. Qi, H. N., et al., Experimental And Theoretical Analysis of Tubular Membrane Aeration for Mammalian Cell Bioreactors. Biotechnol Prog, 2003. 19: p. 1183-1189.
13. Zhang, S., A. Handa-Corrigan, and R. E. Spier, *A Comparison of Oxygenation Methods for High-Density Perfusion Cultures of Animal Cells*. Biotechnology and Bioengineering, 1993. 41: p. 685-692.
14. Orgill, J. J., et al., A comparison of mass transfer coefficients between trickle-bed, hollow fiber membrane and stirred tank reactors. Bioresour Technol, 2013. 133: p. 340-6.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

The invention claimed is:

1. A method of culturing Chinese Hamster Ovary (CHO) cells in a bioreactor comprising providing a mass transfer of a gas to/from the bioreactor without generating bubbles inside the bioreactor, wherein the mass transfer of gas to/from the bioreactor is provided by two or more gas transfer modules comprising a plurality of hollow fibers, wherein at least one gas transfer module comprises an oxygen flow path through the hollow fibers and a cell culture medium flow path around the hollow fibers separated by a non-porous membrane comprising PDMS and wherein at least one gas transfer module comprises an air/carbon dioxide flow path through the hollow fibers and a cell culture medium flow path around the hollow fibers separated by a non-porous membrane comprising PDMS; wherein the bioreactor is a perfusion bioreactor, and wherein the bioreactor comprises a CHO cell density of at least $20 \times 10^6$ cells/ml.

2. The method of claim 1, wherein the two or more gas transfer modules are located outside of the bioreactor.

3. The method of claim 2, wherein the flow of cell culture media and/or cells comprises tangential, axial flow or a combination thereof.

4. The method of claim 2, wherein the flow of the cell culture media and/or cells is at a rate that is sufficient to maintain culture homogeneity without causing shear forces on the cells.

5. The method of claim 1, wherein the plurality of hollow fibers provide a flow path for culture media and cells to travel through spaces separating the hollow fibers.

6. The method of claim 5, wherein the spaces are homogenous or heterogenous.

7. The method of claim 5, wherein the spaces are of sufficient size to allow passage of a cell without causing shear forces on the cell.

8. The method of claim 5, wherein the spaces comprise a distance of about 15 μm to about 2000 μm.

9. The method of claim 8, wherein the spaces comprise a distance 15-30 μm, 20-40 μm, 30-60 μm, 40-80 μm, 60-120 μm, 80-160 μm, 100-200 μm, 150-300 μm, 200-400 μm, 200-500 μm, 200-600 μm, 200-700 μm, 200-800 μm, 200-900 μm, 200-1000 μm, or 500-2000 μm, or a combination thereof.

10. The method of claim 1, wherein the bioreactor comprises a cell density of about $30 \times 10^6$ cells/ml.

11. The method of claim 1, wherein the method avoids production of foam.

12. The method of claim 1, wherein the bioreactor comprises no headspace or substantially no headspace.

13. The method of claim 1, wherein the method requires no anti-foaming agent during cell culture.

14. The method of claim 1, wherein a dissolved oxygen content in the bioreactor is maintained at around 60%.

15. The method of claim 14, wherein hollow fibers have a wall thickness of 55 μm.

* * * * *